(12) United States Patent
Schmitz

(10) Patent No.: US 11,950,765 B1
(45) Date of Patent: Apr. 9, 2024

(54) HIGHLY MANEUVERABLE SURGICAL CATHETER AND BRONCHOSCOPE

(71) Applicant: Gregory P. Schmitz, Los Gatos, CA (US)

(72) Inventor: Gregory P. Schmitz, Los Gatos, CA (US)

(73) Assignee: Syncrobotix, Inc., Los Gatos, CA (US)

( * ) Notice: Subject to any disclaimer, the term of this patent is extended or adjusted under 35 U.S.C. 154(b) by 0 days.

(21) Appl. No.: 18/324,493

(22) Filed: May 26, 2023

Related U.S. Application Data

(60) Provisional application No. 63/499,218, filed on Apr. 29, 2023.

(51) Int. Cl.

| | | |
|---|---|---|
| *A61B 1/00* | (2006.01) | |
| *A61B 1/005* | (2006.01) | |
| *A61B 1/012* | (2006.01) | |
| *A61B 1/018* | (2006.01) | |
| *A61B 1/05* | (2006.01) | |
| *A61B 1/267* | (2006.01) | |
| *A61B 10/04* | (2006.01) | |
| *A61B 90/00* | (2016.01) | |
| *A61M 25/01* | (2006.01) | |

(52) U.S. Cl.
CPC .......... *A61B 1/0057* (2013.01); *A61B 1/0011* (2013.01); *A61B 1/00149* (2013.01); *A61B 1/0055* (2013.01); *A61B 1/0125* (2013.01); *A61B 1/018* (2013.01); *A61B 1/05* (2013.01); *A61B 1/2676* (2013.01); *A61B 10/04* (2013.01); *A61B 2090/3966* (2016.02); *A61M 25/0138* (2013.01)

(58) Field of Classification Search
CPC . A61B 1/0057; A61B 1/0011; A61B 1/00149; A61B 1/0055; A61B 1/0125; A61B 1/018; A61B 1/05; A61B 1/2676; A61B 2090/3966; A61B 10/04; A61B 1/00147; A61B 1/005–01; A61B 1/00156; A61M 25/0138
USPC .......................................... 600/102, 137, 114
See application file for complete search history.

(56) References Cited

U.S. PATENT DOCUMENTS

| | | | |
|---|---|---|---|
| 5,396,880 A | * 3/1995 | Kagan | A61B 5/032 600/128 |
| 11,033,342 B2 | 6/2021 | Schmitz | |

(Continued)

*Primary Examiner* — Timothy J Neal
*Assistant Examiner* — James Edward Boice
(74) *Attorney, Agent, or Firm* — Stephen E. Zweig

(57) ABSTRACT

Multi-stage catheter device configured to navigate through complex narrow tissue openings such as lung bronchi pathway openings of 3 millimeters or less. The device comprises a proximal catheter portion containing a hollow torque shaft, with a distal catheter portion connected to the proximal portion by a rotatable coupler connected to this hollow shaft. The distal position of the proximal catheter can be controlled by up to four independently controlled proximal stage steering cables positioned outside of the shaft, and the shaft itself can be used to rotate the distal catheter about the rotatable coupler. The position of the distal end of the distal catheter can be further controlled by up to four independently controlled distal stage steering cables positioned inside of the hollow shaft. The device is tipped by a tool plate, which can be equipped with various sensors and other instruments, connected to the outside via other conduits.

20 Claims, 38 Drawing Sheets

(56) References Cited

U.S. PATENT DOCUMENTS

| | | | |
|---|---|---|---|
| 2005/0272975 A1* | 12/2005 | McWeeney | A61M 25/0068 600/172 |
| 2008/0045859 A1* | 2/2008 | Fritsch | A61B 18/148 600/567 |
| 2010/0168511 A1* | 7/2010 | Muni | A61M 25/0152 600/104 |
| 2011/0270229 A1* | 11/2011 | Tanaka | A61M 25/0147 604/528 |
| 2012/0209253 A1* | 8/2012 | Donhowe | A61B 17/00 606/1 |
| 2017/0164971 A1* | 6/2017 | Moretti | A61B 17/221 |
| 2019/0046009 A1* | 2/2019 | Wood | A61B 1/018 |
| 2021/0100627 A1 | 4/2021 | Soper et al. | |
| 2021/0137620 A1 | 5/2021 | Wallace et al. | |
| 2021/0379332 A1* | 12/2021 | Komp | A61M 25/0105 |
| 2022/0087755 A1 | 3/2022 | Romo et al. | |
| 2022/0304550 A1 | 9/2022 | Romo et al. | |
| 2022/0313375 A1 | 10/2022 | Zhang et al. | |

* cited by examiner

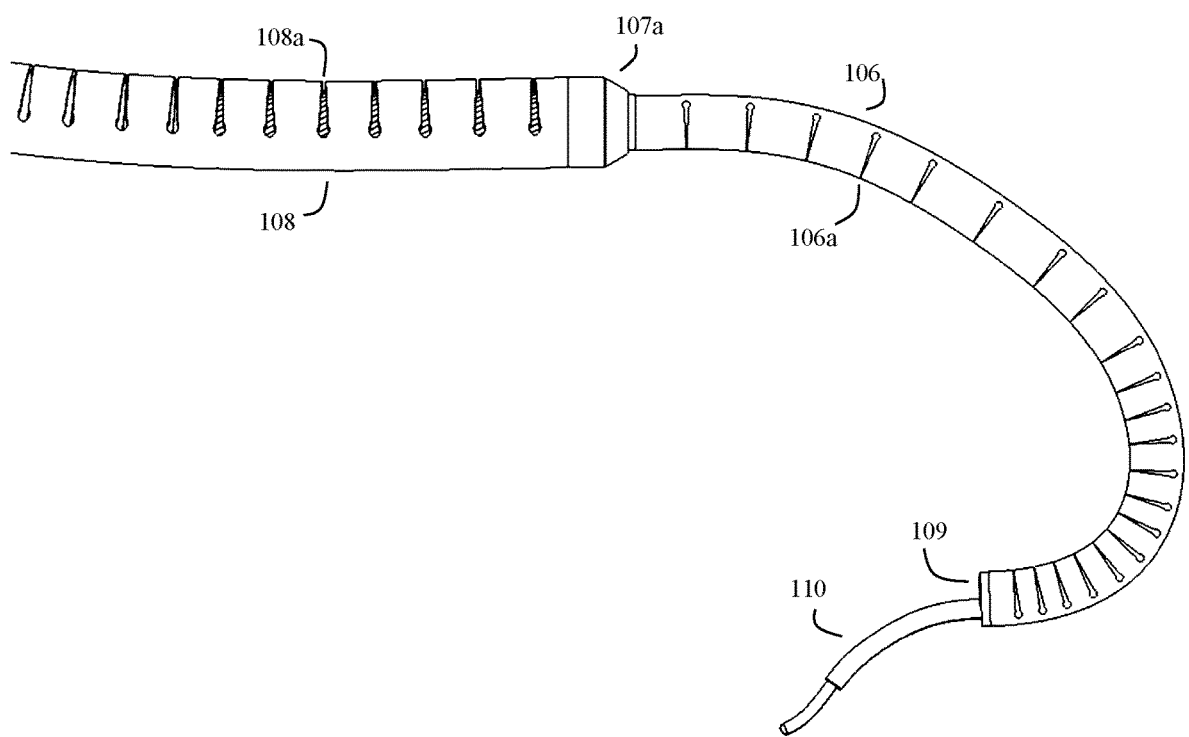

Fig. 12A
Fig. 12B
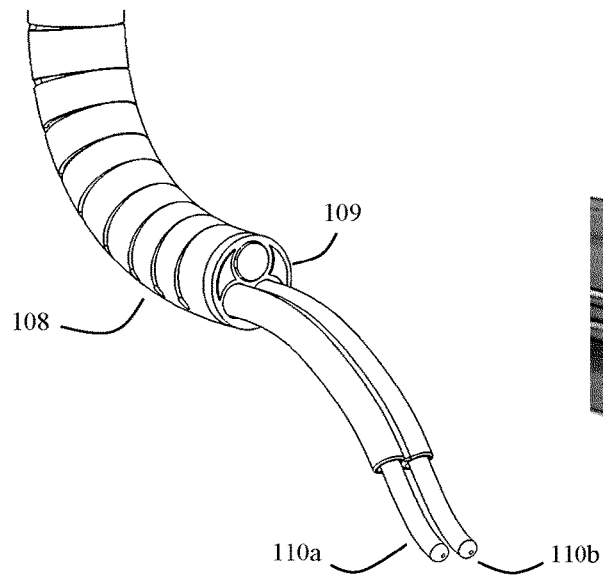
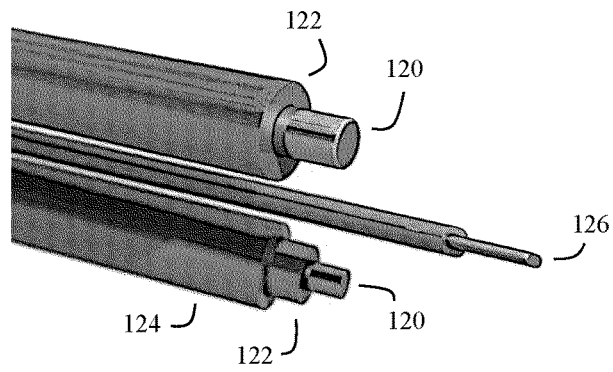

Fig. 38A
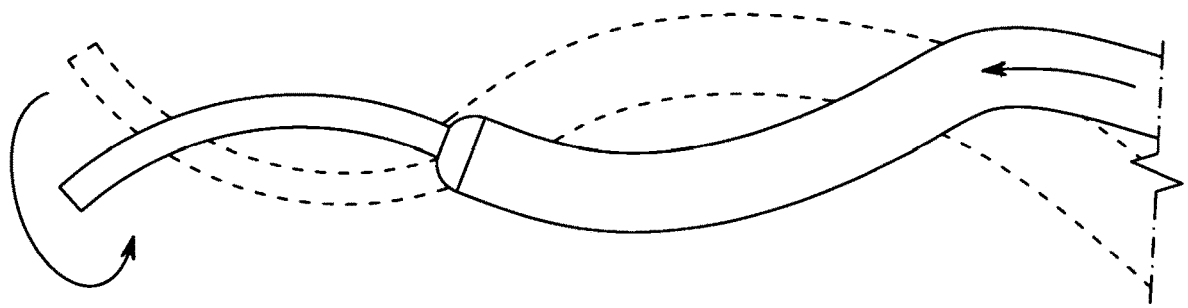
Fig. 38B
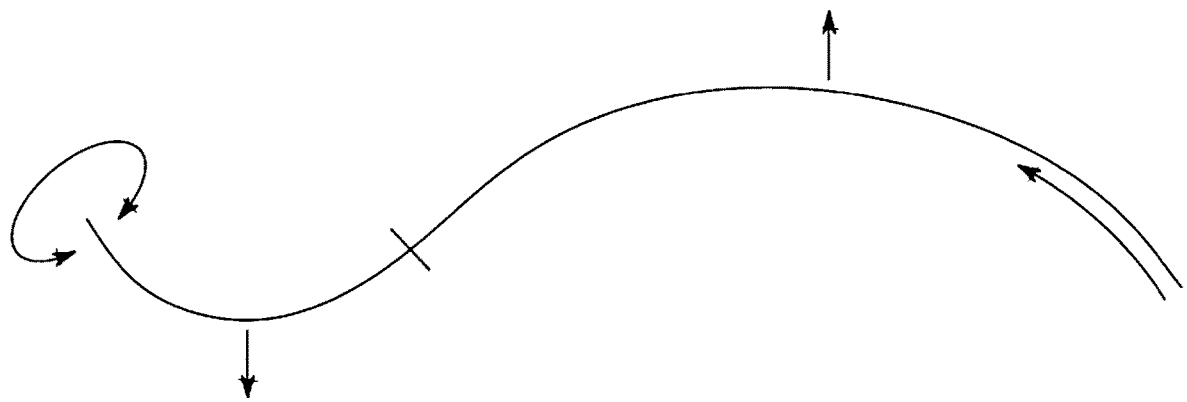
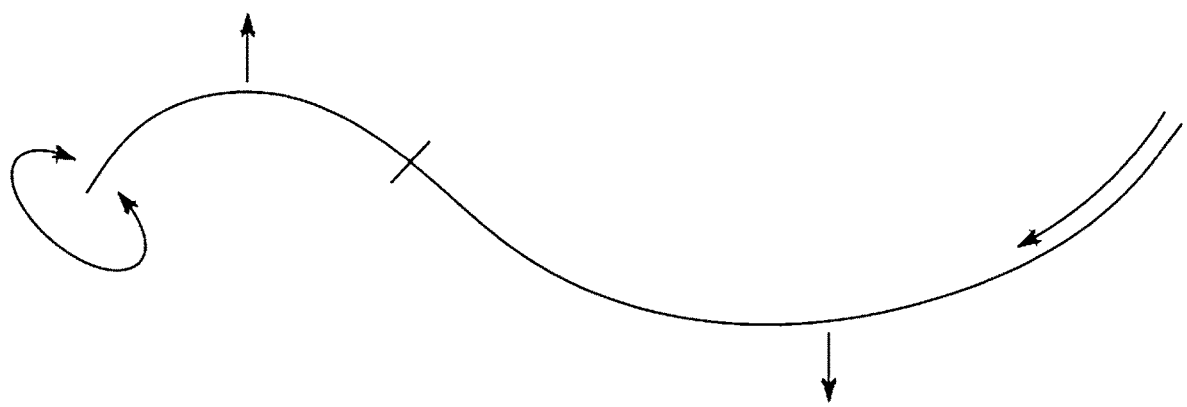

HIGHLY MANEUVERABLE SURGICAL CATHETER AND BRONCHOSCOPE

CROSS-REFERENCE TO RELATED APPLICATIONS

This application claims the priority benefit of U.S. provisional application 63/499,218, filed Apr. 29, 2023. The entire contents of this application are incorporated herein by reference.

BACKGROUND OF THE INVENTION

Field of the Invention

This invention is in the field of surgical catheters and bronchoscopes.

Description of the Related Art

Medical and surgical catheters, and more specialized versions of such catheters such as bronchoscopes, are medical devices that are commonly used for purposes of medical diagnosis and treatment. Such "snake like" devices are designed to traverse various body lumens, such as arteries, veins, portions of the urinary, gastrointestinal, and reproductive systems, as well as various portions of the respiratory system and lungs. These devices are frequently used for other surgical applications as well.

Some of these medical devices are formed from long continuous tubes, often formed from medical grade polymers. Other such devices may comprise articulated sections formed from a plurality of smaller components that are often linked together by flexible joints. Such articulated devices themselves may often then be covered with an optional flexible medical plastic grade polymer as well.

Some of these medical devices are intended for direct manipulation by the surgeon or other healthcare professional. Other such devices may also have various motorized, processor controlled, and even robotically driven accessories. These are often used for greater precision and control.

Examples of such devices include various US patents and patent applications, such as Wallace, US 20210137620 A1; Romo, US 20220087755 A1 and US 20220304550 A1; Zhang US US20220313375A1; Souper US 20210100627 A1; and Schmitz, U.S. Ser. No. 11/033,342 B2.

Other prior art techniques include electroporation. Electroporation is an energy modality of pulsed electric fields in micro and nanosecond domain that if delivered through a micro-bronchoscope, could be used to deliver genes for immune response, initiate necrosis or initiate an immunogenic response.

Despite these advances, further advances in this art would be desirable.

BRIEF SUMMARY OF THE INVENTION

Although the systems and methods disclosed herein can be used for many different medical purposes, the present invention was inspired, in part, by a consideration of difficult-to-treat lung diseases, and the inadequacies of prior art manual and robotic bronchoscopes.

Thus, this disclosure will discuss both the structure of the lungs, and the utility of these improved methods for lung disease, in some detail. Note however, that this extensive discussion of lung structure and improved bronchoscopes is not intended to be limiting. The improved medical devices disclosed herein may be given different names, and may be used for a wide variety of medical and veterinary diagnostic and surgical purposes.

About the Structure of the Lung, and the Limitations of Prior Art Bronchoscopes

The bronchus of the lungs can be viewed as following a natural Fibonacci pattern of a typical tree where the branches divide and reduce in size as they get further out for the main trunk or, in this case, the Trachea. FIG. 1, which shows the lung bronchus system, illustrated shows the size reduction of the bronchial tree as the air moves from the larynx (10), down the Trachea (12), and divides into the Primary Bronchus (14), the Secondary Bronchus (16), the Tertiary Bronchus (18), and lastly the many Bronchiole (20).

The diameter of the bronchus pathways reduces in diameter as the branches move outward and downward away from the Trachea. For example, going from Subsegmental (Tertiary) to Terminal Bronchi (before the Bronchiole), the diameter usually steps down from about 5 mm (millimeter) down to about 1 mm. This results in about a thousand terminal bronchi that are located in in the outer third of the lungs (22). Many lung disorders, such as lung tumors, can occur in this region.

Unfortunately, this outer third portion of the lungs (22) is largely inaccessible to prior art bronchoscopes. This is because prior art bronchoscopes, including robotically driven bronchioscopes, typically have a minimum diameter of 3.5 to 4.2 mm. Such devices are also difficult to maneuver through the many twisting of the bronchial tree, because such devices have limited flexibility (e.g. a limited or large articulation radii).

Prior art bronchoscopes and robotic bronchoscopes have about a 4 mm diameter and an 18-20 mm articulation radius. These prior art bronchoscopes are typically single stage catheters, often of continuous diameter, which are introduced into the lung with the aid of an introducer sheath. Occasionally medical practitioners attach a 19-22 gauge (~1 mm) flexible nitinol needle to the distal tip of the bronchoscope, and use this wire tip to reach still further into the lungs for lesion biopsy. However, such wire tips have limited flexibility and maneuverability (limited articulation), and are thus often unsatisfactory for this purpose. At a bronchial diameter of 4 mm, there are roughly 50 bronchi that can be accessed with prior art robotic bronchoscopes. As the bronchial diameter reduces to 3 mm, there are roughly 100 bronchi that can be accessed with with a 3 mm robotic bronchoscope, if one existed.

The invention is based, in part, on the insight that improved bronchoscopes with diameters below 3 mm can provide a 6 to 20 fold greater opportunity to detect and treat currently inaccessible cancerous lesions in the outer third of the lung. So at 3 mm, we in effect have a "biometric transition point" where prior art bronchioscopes fail, to proceed further along the ever smaller diameter lung bronchi.

- 3 mm diameter bronchioscope could access about 100 currently inaccessible bronchi
- 2.5 mm diameter bronchioscope could access about 300 currently inaccessible bronchi
- 1 mm diameter bronchioscope could access about 1000 currently inaccessible bronchi The invention is based on the further insight that using prior art flexible needles to extend the range is not adequate because such needles are not actively steerable. Such needles have a high risk of tearing through delicate vascular structures, because their trajectory will be approximately a straight path when they exit the prior art bronchoscope.

The invention is also based, in part, on the insight that what is needed is an improved bronchioscope, such as a two (or more) stage broncoscope, capable of extremely narrow distal diameters, as well as an ability to be precision driven. In some embodiments, this improved device may also utilize an introducer sheath, and be capable of having both stages that are robotically driven along the same axis.

FIG. 2 shows a close up of the various lung bronchus and bronchi pathways, showing the path transition points (104) where a second, narrower, stage of a two stage bronchoscope (100) can extend out from a wider first stage (See FIG. 3). The wider first stage (106) can guide the device through the larger diameter bronchus pathways, and position the narrower second stage (108) to then proceed further through the ever narrowing segmental bronchi and into the appropriate bronchiole nearest the target (often a potential lesion or tumor).

The challenges of such an improved device should be appreciated. As can be seen from FIG. 2, the bronchi branches take many sharp turns. For best performance, the improved bronchioscope device needs to articulate and navigate these ever smaller diameter paths. Thus again, at the Tertiary or Subsegmental Bronchi (3-6 mm diameter, 18), there are about 38 branches. But when the device is traversed beyond the 3 mm Tertiary branches, there are potentially a thousand or more 1000 branches in the Terminal Bronchi (the outer $1/3^{rd}$ of the lungs 22). Ideally, the design would allow the operator to articulate or manipulate the tip of the bronchioscope through each branch, without punching through or otherwise damaging the delicate vascular structures and/or bronchus walls.

The invention was also inspired, in part, on the insight that such an improved device should be able to do useful work once it reaches its destination. This includes an ability to position useful sensors, such as cameras and lighting systems, obtain tissue biopsies, and administer effective therapy to tissue targets positioned at such difficult to reach locations.

BRIEF DESCRIPTION OF THE DRAWINGS

FIG. 11 shows how the flexible sections can be tailored to a patient's particular bronchi where the lesion location may be a more challenging area to reach due to some non-conformity FIG. 12A and FIG. 12B show the use of optional electrodes

FIG. 38A and FIG. 38B shows an example of a robotic drive algorithm that drives the motors to create a wave between the distal and proximal stages. The distal stage is also rotating/threading itself into the bronchus.

DETAILED DESCRIPTION OF THE INVENTION

Figure 1:
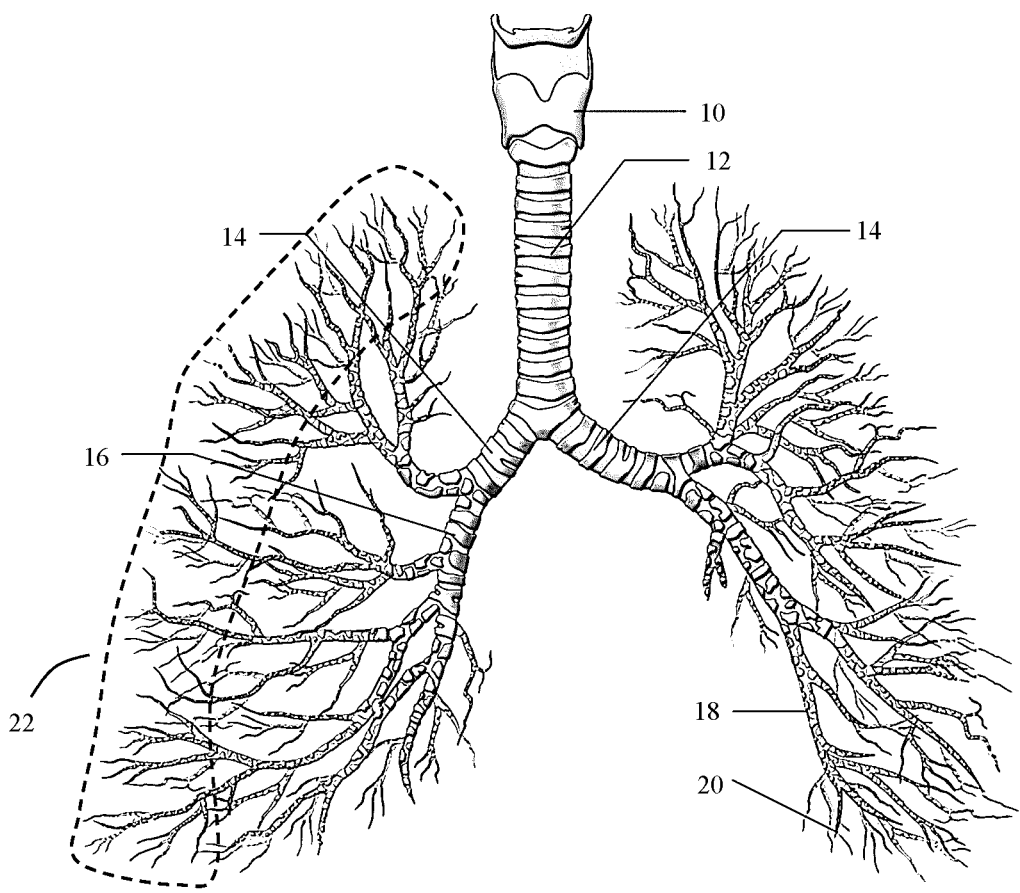
FIG. 1 shows the lung bronchus system.

There is a need to improve surgical procedures by reaching further into a particular area of the body with the most minimally invasive approaches. In all instances, the body's internal pathways follow a sequence of narrowing branches. The further down the branch or vessel, the narrower the internal pathway becomes. This creates many challenges for engineers. It pushes the creative and technological limits.

Catheter development is dependent on efficient implementation of metals, polymers, and semiconductors. Metals provide for higher stress limits and thus smaller parts which enable the production of smaller tools. Stainless and Nitinol metals are used in the skeleton of catheters and micromechanical tools. Polymers are used for the skin and insulation of the catheter, allowing smooth interaction between the tool and the body's pathways. Silicon provides the sensing and feedback for producing smart embedded devices at the distal portion of the catheter. Other electronic embedded elements can include video cameras, such CMOS cameras, and LED lighting. The CMOS camera and pico-LEDs provide an important advantage by allowing more flexibility (less resistance) at the distal lead and along the catheter's length. This is due to the braided electrical wires for power, return and communication leads. Whereas fiber optic scopes and fiber optic lighting limit the radius of bend or articulation angle of the catheter due to the higher bending resistance of the glass fibers.

Advances in robotics and visualization systems are creating new opportunities in medicine. These new opportunities create advantages over manual driven instruments. Stability is one of the advantages, and this is something easily recognizable when traditional manual surgical tools are attached to the robot. When catheters are robotically driven, several advantages can be leveraged: semi or full autonomous pathfinding, a locked position, drive methods for traversing further, and tracking position relative to the target with a real time C-arm surgical imaging device (CT or MRI).

Applying robotics to a catheter exhibits many challenges. Cost and performance must be well balanced due to a disposable cost model. New ideas that approach design for manufacturing (DFM) and cost from the initial challenge push both the creative and technological potentials.

The invention described tackles these challenges by exploiting advanced techniques in micro tool development coupled with robotics and visualization technology.

About nomenclature: in this disclosure, the invention will alternately be described as the invention, the device, the catheter, the bronchoscope, and even the robotically driven articulated bronchoscope. These terms are interconvertible, and the use of any given term in a specific context is not intended to be limiting.

Description of Applications (Curing Pulmonary Diseases)

Robotic procedures along with advances in real-time computer visualization of the body have opened entirely new approaches to targeting and curing many diseases. One such area is in the diagnosis and treatment of lung cancer. Most lung lesions are in the periphery of the lungs. Seventy percent of lung lesions are in the outer third of the lungs. This is a huge opportunity for applying micro-invasive technologies due to the narrowing of the bronchus in the periphery.

Current detection and treatment are limited by several shortcomings even with the application of robotics. For robotic bronchoscopy, the catheter technology is limited by cost constraints of the disposable, and this directly impacts the catheter size and mobility. Making devices smaller comes with many challenges which, if not approached carefully, can create cost and performance disadvantages.

These constraints provide a unique opportunity for innovation. It is achievable to reach and treat currently inaccessible lesions in the outer third of the lungs by applying creative methods of manufacturing. It is possible to develop a highly mobile sub 3 mm robotic micro-bronchoscope with the ability to safely target the outer third of the lungs. This is an area of the lungs where a thoracic surgeon must apply a biopsy needle under fluoroscopy by going transthoracic to obtain a tissue sample. Although this is the standard of care for the hard-to-reach areas of the lungs, it comes at a price with a pneumothorax rate of 20%. Additionally, this procedure does not provide a targeted treatment or cure if the lesion is found to be cancerous. It is only a diagnostic method. The cost of treating a 20% pneumothorax rate is a huge issue and a great opportunity for developing better methods of treatment.

The outer third of the lungs (22) is where 70% of lung lesions are located. Going translumenal from the bronchus to the outer third provides the opportunity during the same procedure to biopsy (detect) and treat the lesion if found to be cancerous. In addition to detecting and treating cancer, other illnesses such as chronic bronchitis could be treated with electroporation to illicit an immunogenic response. Another application would be targeted micro-lung-lavage at the Alveoli.

Figure 2:
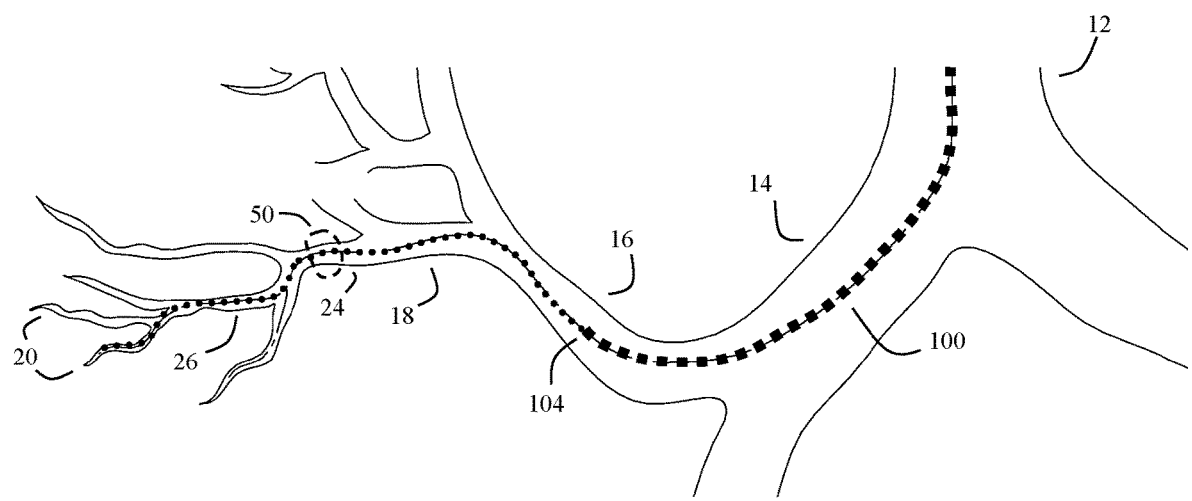
FIG. 2 shows the various bronchi structures and pathways

FIG. 2 shows the trajectory paths from Primary (14) to Secondary (16) and then at the end of the Tertiary branch (18) where the pathway narrows to <3 mm in the subsegmental Bronchi. This is the transition to Terminal Bronchi. The thick dashed or broken line represents the path of a Bronchoscope (100). Along the scope's path, transition points are labeled. These points are labeled "End of Introducer Path" (104), "End of Proximal Path" (24), "Biometric Transition Point" (50), and "Distal Stage Path" (26). These labels represent some of the key areas along the length of the endoluminal catheter that is disclosed in this application.

As previously discussed, prior art robotic bronchoscopes have a diameter of about 4 mm, and also have about a 18-20 mm articulation radius (turning radius). Although, in some prior art situations, a 19-22 gauge (~1 mm diameter) flexible nitinol needle can be attached to the tip of the bronchoscope for lesion biopsy, such needles are difficult to steer, and tend to be unsatisfactory for many purposes.

Figure 3:
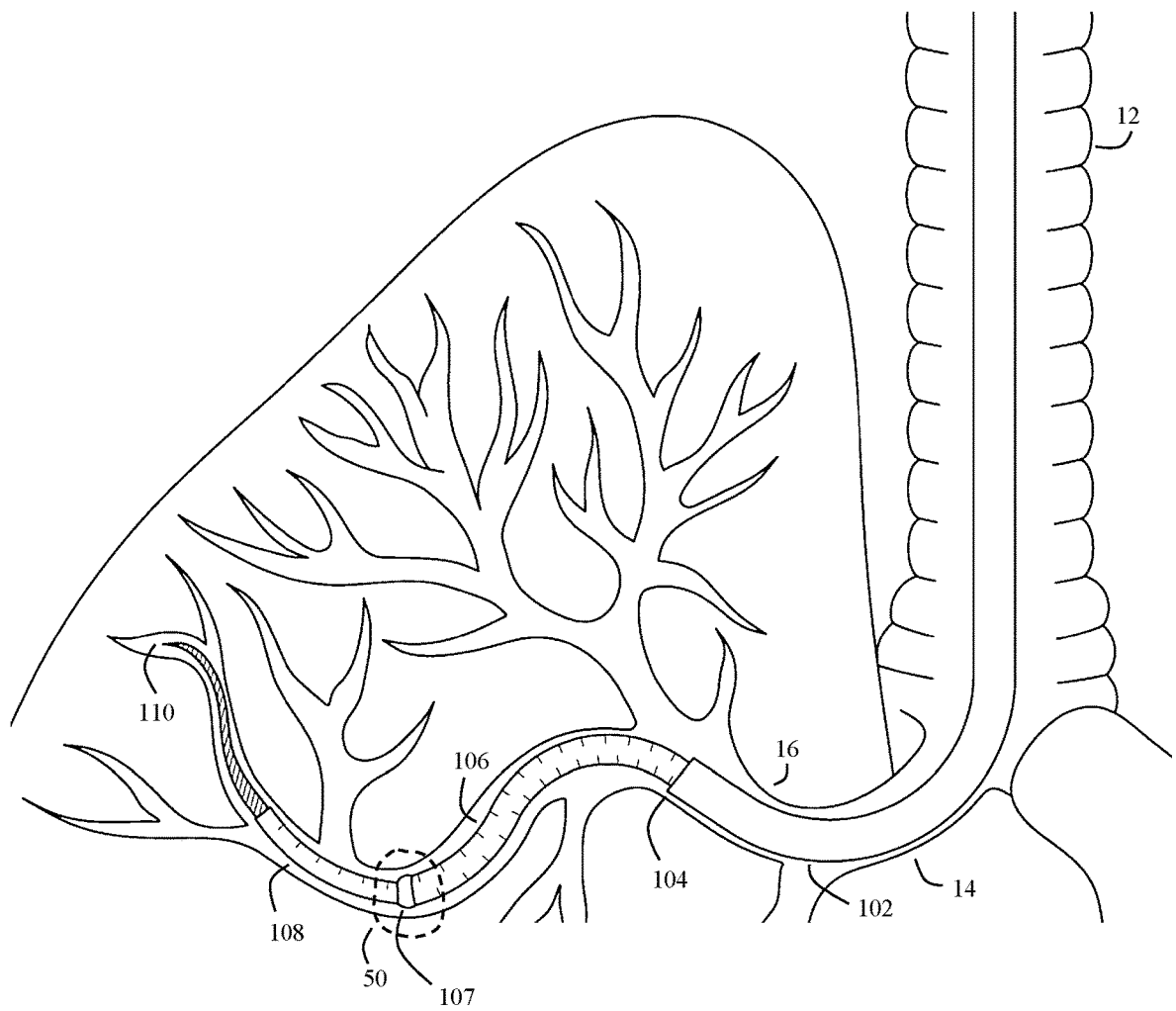
FIG. 3 a hypothetical path for the invention's bronchoscope reaching the outer ⅓rd of a lung.

Based on the trajectory path in FIG. 2 and FIG. 3, the "Biometric Transition Point" (50) can be viewed as being the region of the lungs with bronchus and bronchi diameter of 3 mm or less, where prior art bronchoscopes stop.

As previously discussed, in some embodiments, the invention may be a two (or more) stage broncoscope with an introducer sheath (102) where both stages (106) and (108) are robotically driven along the same axis. FIG. 3 shows a close up of the path transition points that show where this two stage bronchoscope is divided (based on biometric data).

This is the challenge, especially where the bronchi branches take sharp turns. The narrowing of pathways below 3 mm diameter (50), creates a huge opportunity for an improved bronchoscope that can articulate and navigate these smaller diameter paths. For Tertiary or Subsegmental Bronchi (3-6 mm), there are 38 branches. When the bronchioscope is traversed beyond the 3 mm Tertiary branches (50), the opportunity rises to 1000 branches in the Terminal Bronchi (the outer third of the lungs 22). Beyond the Tertiary branches, this can be viewed as being biometric transition in the design of the two stage bronchoscope. The improved device and methods disclosed herein are designed to penetrate this (3 mm diameter or less) region of the lungs (22), which is generally inaccessible to prior art manual or robotic bronchioscopes.

FIG. 3 shows the four main components of this improved catheter system: These are the introducer sheath (102), the proximal stage (106), the distal stage (108), and the probe or tool (110). At (107), there is a transition point where the proximal stage (106) is coupled to the distal stage (108). As will be discussed in more detail shortly, this coupling allows for the rotation of the distal stage (108) relative to (or about) the proximal stage (106). As can be seen in FIG. 3, the distal stage (108) typically has a much smaller outer diameter (OD) than the proximal stage (106). The device is often configured so that the surgeon or robot can manipulate the primary stage (106) and coupler or transition region (107) near the biometric transition point (50), and then use the distal stage (108) to proceed further into outer third of the lungs (22) or other difficult to access region.

In a preferred embodiment, the surgeon, with or without robotic assistance, will often manipulate (106), (107), and (108) in synchrony to get to a desired location near the target. Then a tool or probe, such as (110), may then slide out and extend to the target.

Figure 4:
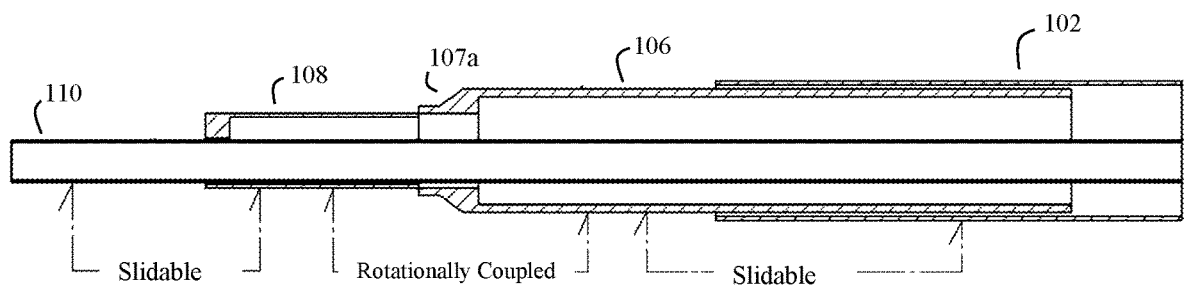
FIG. 4 shows a schematic cross-sectional view of the device's distal and proximal stages, showing where they are coupled, and how the distal stage is driven to rotate and flex relative to the proximal stage.

FIG. 4 shows a schematic cross-sectional view of the distal (108) and proximal stages (106) where they are coupled (107), and where the distal stage can be driven to both rotate and flex (relative to the proximal stage). Both stages can be slid into the lungs or other body lumen through the introducer sheath (102). Various tools and probes (110) can be extended (either manually or robotically) out of the end of the distal stage. The distal and proximal stages are typically configured to be slidable in the steerable introducer sheath (102), and the tools or probe devices are slidable (e.g., can slide in and out of) in the distal and proximal stages.

Figure 5:
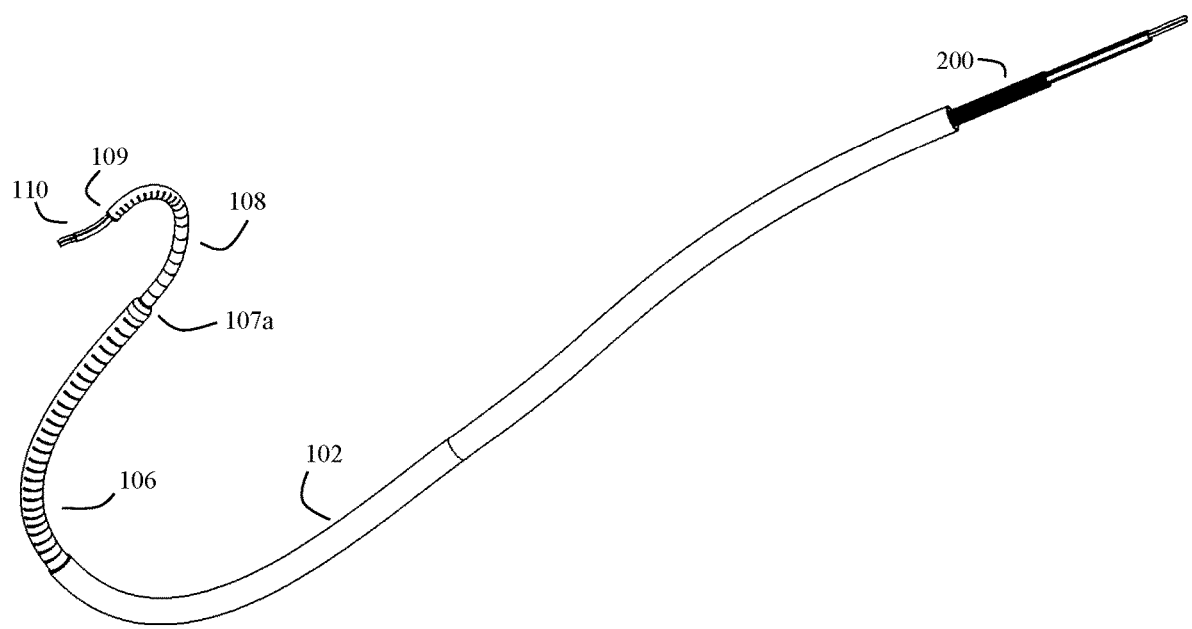
FIG. 5 shows another view of the device.

FIG. 5 shows another view of the dual stage articulating rotary robotic bronchoscope. The distal stage (108) can rotate about the proximal stage (106). This feature allows simple single plane flexible catheter portion to rotate at the distal end, thus giving it full 3-dimensional range of motion and maximizing the devices inner diameter (ID) for various devices such as camera, lighting, and tools while minimizing the devices outer diameter (OD).

Other features shown on FIG. 5 will be discussed in more detail shortly.

As will be discussed in more detail shortly, in some embodiments, the invention may be a multi-stage catheter device. This device can comprise a distal stage hollow catheter (108) and a proximal stage hollow catheter (106), one end of this distal stage hollow catheter affixed to an end of the proximal stage hollow catheter by a hollow rotatable coupler (107b, also called a rotary joint) and transition housing (107a) configured to enable the one end of the distal stage hollow catheter (108) to rotate with respect to the end of the proximal stage hollow catheter (106). In some embodiments, the rotary joint (107b) and housing (107a) may be configured to be capable of being moved to at or near the biometric transition point (50).

The device will usually further comprise a hollow torque shaft (200) mounted inside the proximal stage hollow catheter. This hollow torque shaft is configured (200) to convey torque to the distal stage hollow catheter (108).

The device typically further comprises various conduits. These can comprise at least one proximal stage steering cable (210) connected to the transition housing (107a). This at least one proximal stage steering cable (210) is disposed inside the proximal stage hollow catheter (106), but outside the hollow torque shaft (200). This at least one proximal stage steering cable (210) is configured (or enabled) to convey proximal stage steering force on the transition housing (107a). This configuration causes the transition housing (107a) and the distal stage hollow catheter (108) to move according to the proximal stage steering force.

Figure 16:
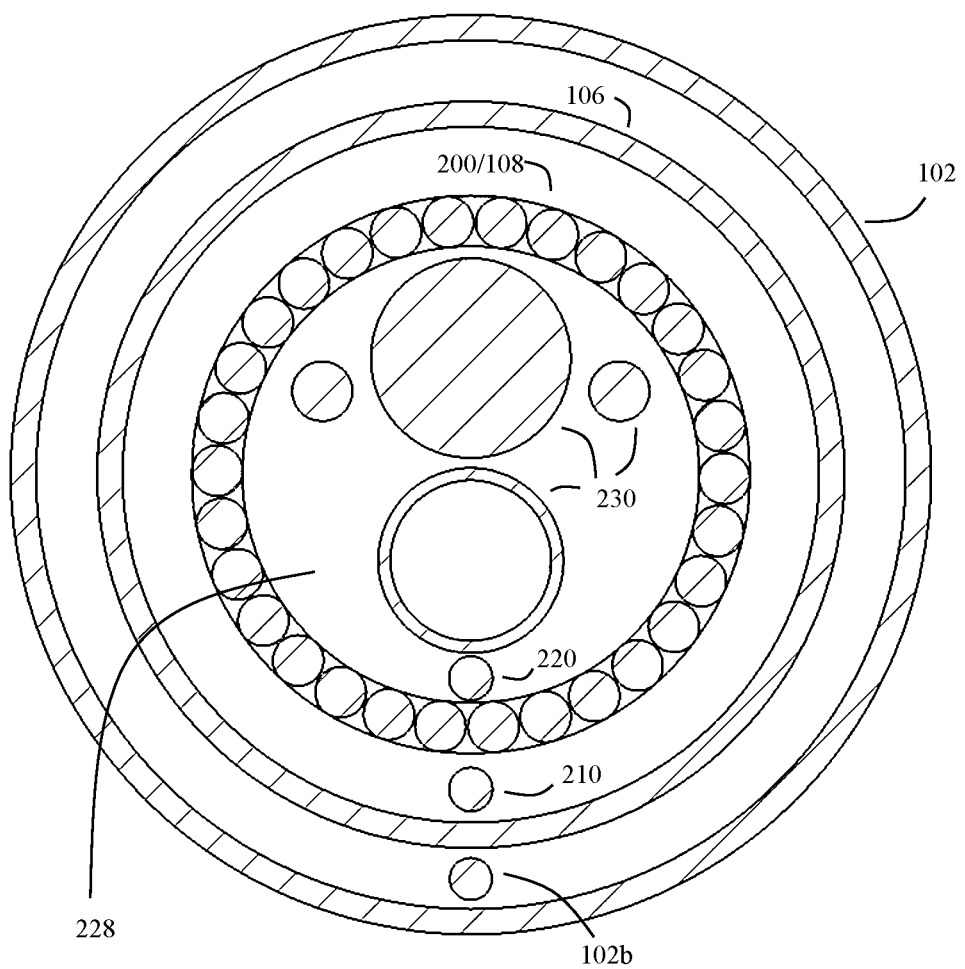
FIG. 16 shows a cross section of the system using a 1-way Steerable Introducer Sheath, 1-way Proximal Stage, 1-Way Distal Stage with Torque Steering.

As shown in FIG. 5, FIGS. 6A and 6B, and FIG. 16, The hollow torque shaft (200), the distal stage hollow catheter (108), the hollow rotatable coupler (107b) and the transition housing (107a) are further configured to comprise a working channel (FIG. 16, 228). This working channel configured to convey a plurality of other conduits through the proximal stage hollow catheter (106) and the distal stage hollow catheter (108) to at least a distal tool plate (109). This plate is mounted on a distal end of the distal stage hollow catheter (108).

Note that in some embodiments, (See FIG. 9B, and FIG. 27) at least some of these other conduits comprise at least one distal stage steering cable (220). These cables are connected to the distal tool plate (109) on the distal end of the distal stage hollow catheter (108). These distal stage steering cables (220, and optionally also 222, 224, and 226) are configured (or enabled) to convey distal stage steering force on (or to) the distal tool plate (109). This configuration causes the distal tool plate (109) and the distal stage catheter (108) to move according to the distal stage steering force.

Figure 6A:
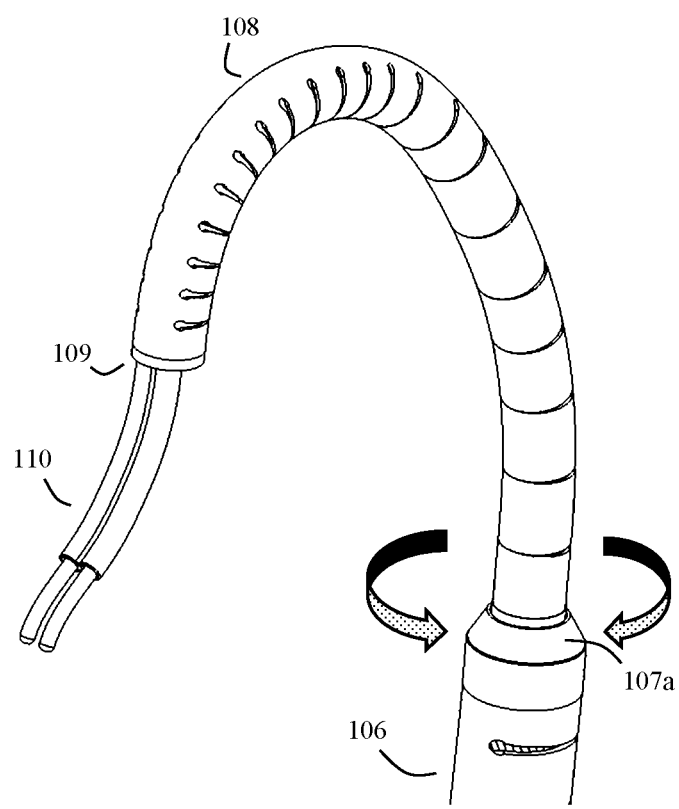
FIG. 6A and FIG. 6B show how the distal stage can rotate via a torque shaft while flexed to a curved position.
Figure 6B:
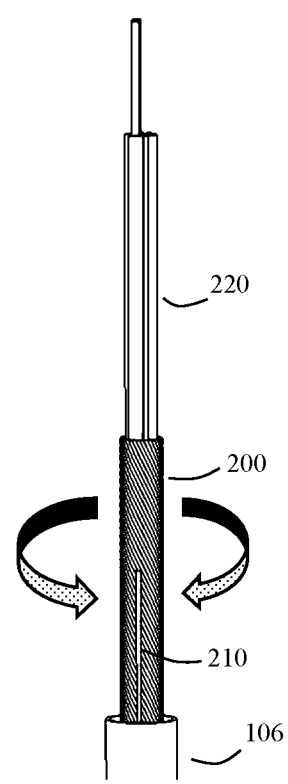

FIG. 6A and FIG. 6B show how the distal stage can rotate via a torque shaft while flexed to a curved position.

The torque shaft is rotated (200) while the proximal stage (106) is constrained from rotation. This torque is transmitted down the flexible shaft (200) with optimal torque transmission properties over long distances. The transmitted torque reaches the transition housing (107a) where it is transmitted to a coupler (107b) which causes the distal stage (108) to rotate.

When actuating the rotational portion of the distal stage (106), motor control can be used to help reduce the friction between coupler (107a, 107b) and the housing and proximal stage by quickly lowering cable tension (210) and pulsing the torque shaft (200) at a high rate of repetition. This force dithering technique is very important in rotating/actuating the small diameter distal stage over long distances as described.

Figure 7:
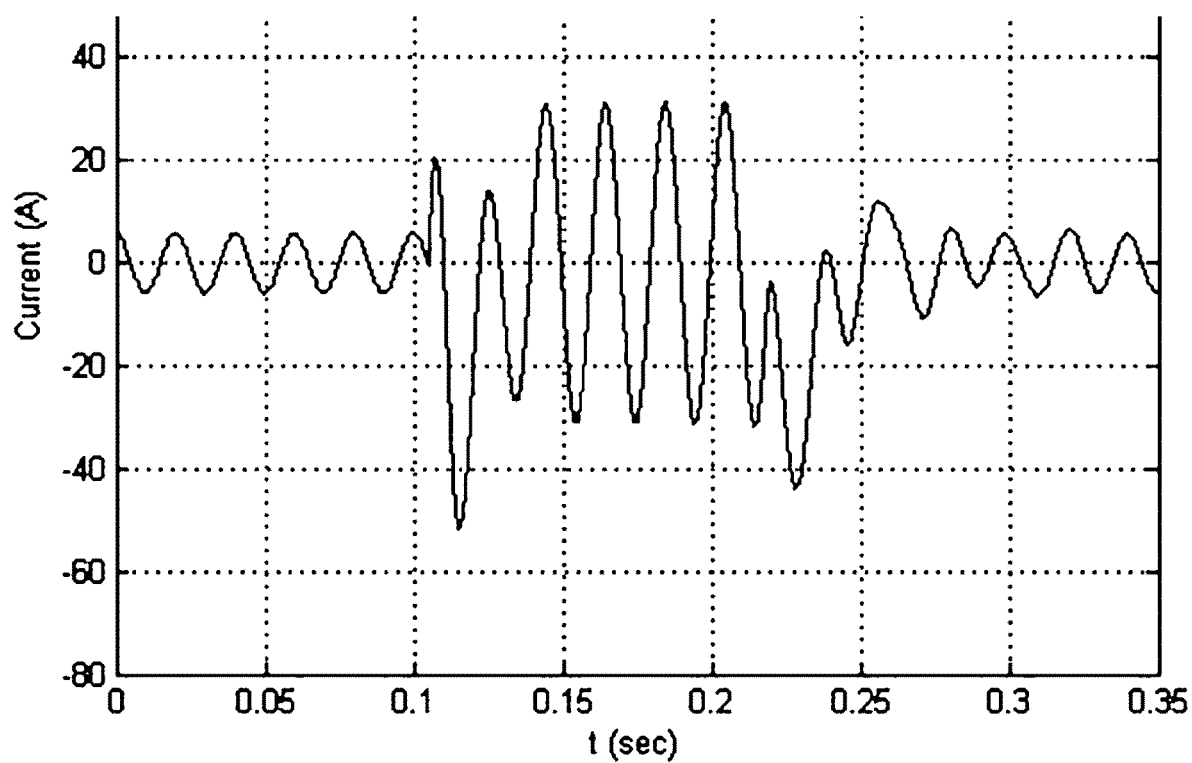
FIG. 7 shows the ripple drive waveform used by the drive amplifiers for breaking the frictional force and rotating/actuating the distal stage torque shaft.

FIG. 7 shows the ripple drive waveform that may be used by the motor/actuator drive amplifiers for breaking the frictional force and rotating/actuating the distal stage torque shaft (200).

Put alternatively, in some embodiments, the device can further comprise a computerized motor actuator system (See FIG. 20-21, 306, M) configured to apply variable torque to the hollow torque shaft (200). This motor actuator system can also be configured to provide variable tension to any of the proximal stage steering cables (210, and optionally also 212, 214, and 216) and/or the distal stage steering cables (220, and optionally 222, 224, and 226). In some embodiments, a given actuator (motorized actuator) can comprise multiple components, such as a drive wheel (306) and a motor (M). Depending on the embodiment, these components may be combined or separated, but for simplicity, here we will usually refer to these components as actuators. In any event, the actuator will usually translate a control signal (often from a computer processor) into a mechanical displacement (often of a conduit such as a steering cable).

FIG. 7 shows the ripple drive waveform that may be used by the drive amplifiers for the actuator system (306, M) for breaking the frictional force and rotating/actuating the distal stage torque shaft (200).

In some embodiments, the computerized motor actuator system (306, M) may operate according to an algorithm configured to reduce friction, while still guiding the catheter to a desired location. This algorithm may operate by repetitively lowering the variable tension (on cables 210 . . . 216 or 220 . . . 226) to first reduce friction. Then the actuator may apply torque (on the shaft 200) to partially rotate the distal stage hollow catheter (108). The algorithm may then reestablish tension (by increasing tension on cables 210 . . . 216 or 220 . . . 226) to guide the catheter to the desired location. In a preferred embodiment, the algorithm is configured to impart a rapid change in tension and torque so as to produce a smooth controlled actuation of the distal stage.

Figure 8:
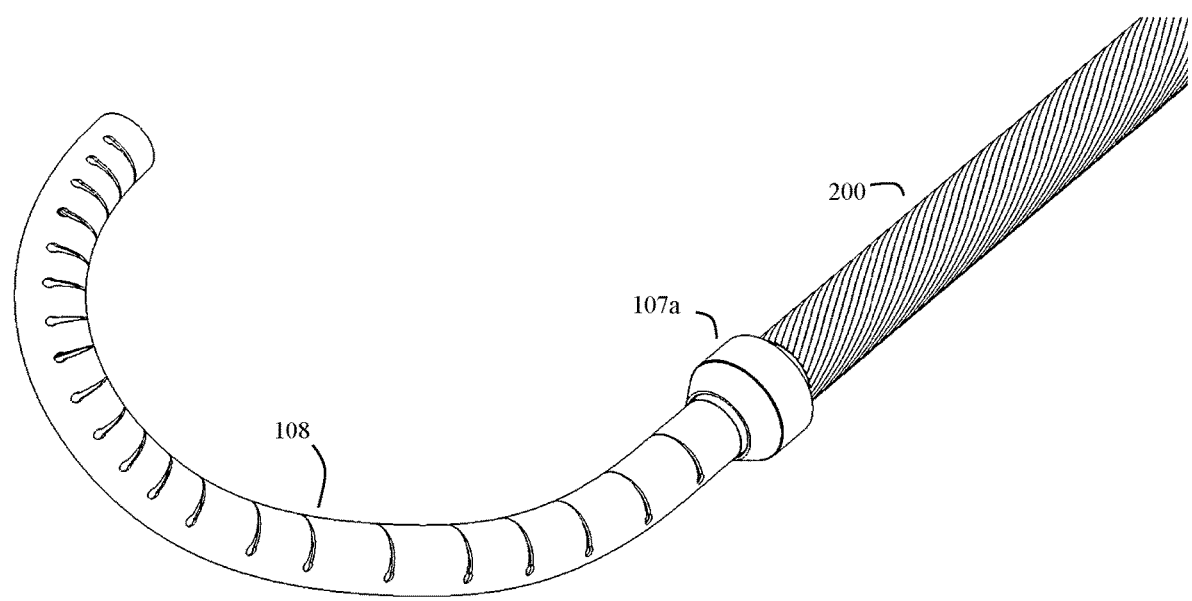
FIG. 8 shows the details of the distal stage with its torque shaft (multi-filar) exposed

FIG. 8 shows the details of the distal stage with its torque shaft (200, here composed of multiple strands) exposed (this would normally be hidden by the proximal stage 106, here not shown). The torsion steering drive tube (also called shaft 200) is made up of an array of wires arranged circumferentially with an angle of twist or spiral where each wire runs the full length of the catheter without interruption. This continuous arrangement of wires transmits torque with the least amount of hysteresis while allowing the shaft to be flexible.

Figure 9A:
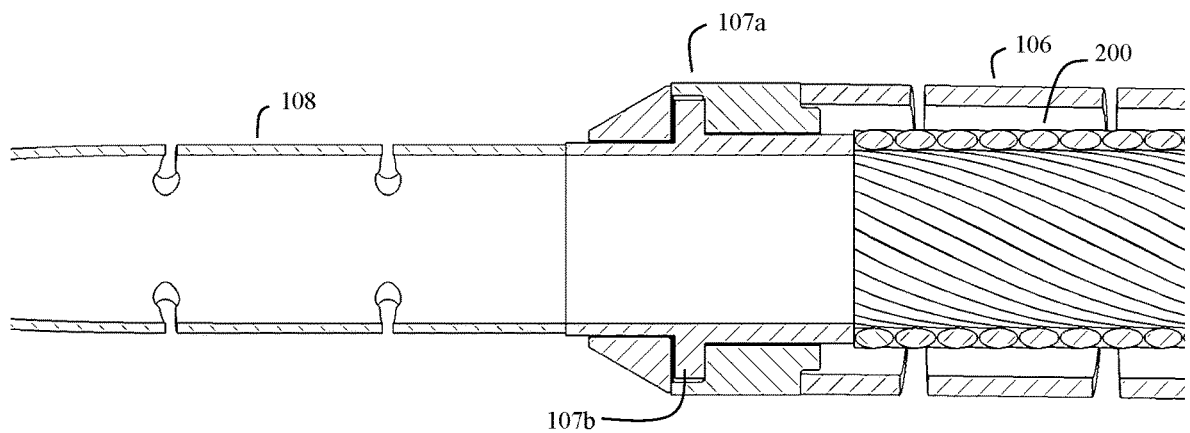
FIG. 9A shows a cut section of the transition housing and how torque is applied to the to the distal stage while the proximal stage remains stationary.

FIG. 9A shows a cut section of the transition housing (107a), showing how the drive shaft (200) applies torque to the distal stage (108), while the proximal stage (106) remains stationary. Note that often, the transition housing (107a) also comprises a rotating section (107b), called the hollow rotatable coupler, that is attached to both the distal stage (108) and the torque shaft (200). In general, unless otherwise specified, assume that the transition housing (107a) also includes the hollow rotatable coupler (107b).

Note that in some embodiments, the torque shaft (200) can alternatively be made from a laser cut hypo-tube such that is it flexible and also able to transmit torque. As another alternative, the torque shaft (200) can also be made from a metal or plastic fiber braided sheath and covered in a pliable polymer.

Figure 9B:
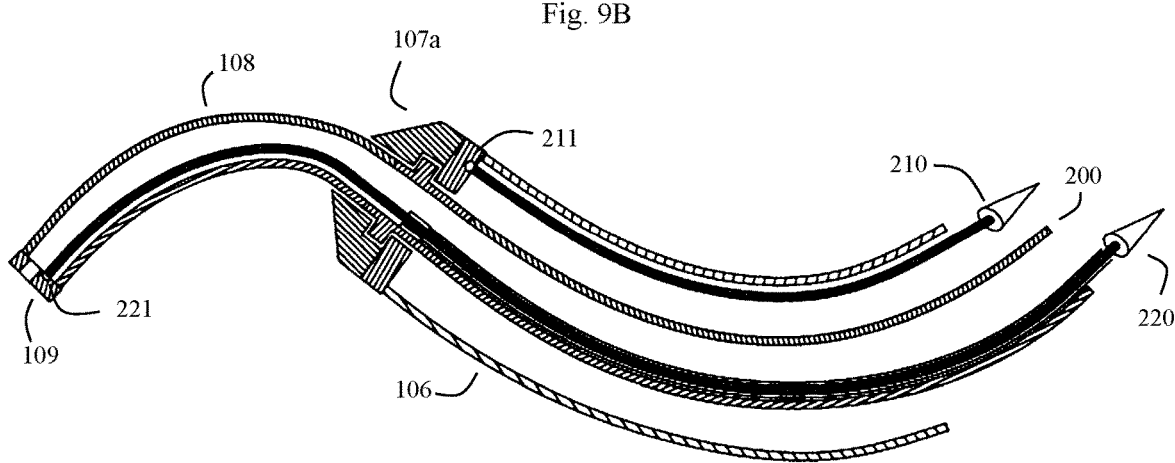
FIG. 9B shows a cut section of the transition housing, also showing how the conduits operate

FIG. 9B shows a cut section of the transition housing, also showing how the conduits (here cables 210 and 220) operate. Here conduit (210) is configured as a proximal stage steering cable. That is, the conduit or steering cable is disposed inside the proximal stage hollow catheter (106), but outside the hollow torque shaft (200). It is configured to convey proximal stage steering force on the transition housing (107a), here by attachment point (221). By contrast, conduit (220) is configured as a distal stage steering cable.

Figure 10:
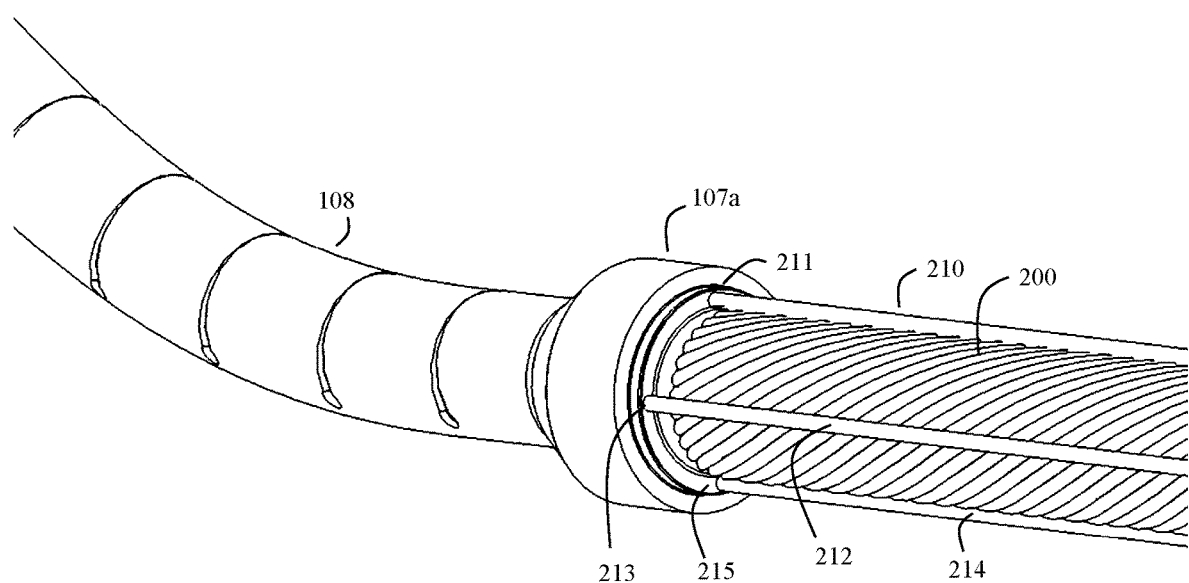
FIG. 10 shows how the proximal steering cables are attached to the transition housing. These cables run the length of the proximal stage all the way up to the drive mechanism.

FIG. 10 shows a further detail of how the conduits may be proximal steering cables (here four cables 210, 212, 214) can be attached to the transition housing (107a) at connection points (211, 213, and 214). These cables run the length of the proximal stage (106, not shown) all the way up to the drive mechanism.

FIG. 11 shows how the flexible sections (106 and 108) can be tailored (e.g., custom manufactured) to better fit a patient's particular bronchi where the lesion location (e.g., target) may be a more challenging area to reach due to some pathway non-conformity.

FIG. 11 also shows that any of the distal stage hollow catheter (108) and the proximal stage hollow catheter (106) may further comprise a plurality of slits (such as 108a, 106a) along at least a portion of their circumference. These slits may have positions and dimensions that are configured to facilitate catheter traversal through a series of branching body lumens of progressively smaller internal diameters.

As will be discussed later (see FIGS. 39 and 40), in some embodiments, the structure of a patient's particular pathway may be obtained by scanning (e.g., by using a C-arm medical imaging scanner or other type scanner to scan the patient, and to create a computed 3D model of the patient). This computed 3D model can be generated before surgery. This pathway data from the model can be used to determine the ideal trajectory of the distal stage (108). This distal stage design could be automatically generated, such as by standard computer processor or AI methods, using current patient scans. (e.g., CT/MRS generated 3D models and historical data/3D scans). This data can be used to determine exactly how to construct the distribution and flexibility of any optional flexure joints (108a, 106a) along the distal and proximal stages (106, 108), as well as the length of the distal and proximal stages.

FIG. 12A and FIG. 12 B show the use of optional electrodes, such as (110a and 110b), here shown extending out of distal plate (109). In some embodiments, bipolar (e.g., two) electrodes may be used for targeted treatment, and can be used to deliver high frequency electrical energy from a suitable source. These micro electrodes (110a, 110b) can be isolated from one another by an insulating lumen. In some embodiments, the electrodes may be made from DFT® wire (Drawn Filled Tubing). Such DFT wire may comprise a gold core electrode (120) surrounded by nitinol (122), and often then an insulator (124). This allows for elasticity and conductivity to be optimized in small diameter wire<1 mm. More conventional wires, such as insulated copper wires, may also be used (126). In some embodiments, these wires will also have radiopacity for viewing position of electrodes during a real-time C-Arm CT scan or other imaging process.

Thus, although some of the conduits may often comprise tension or steering cables such as (210), and (220), at least some of the conduits may also comprise electrical conduits (such as 110a, 110b). These electrical conduits may be used to transmit any of electrical power or electrical signals to any of probes, sensors, or other electrically activated devices disposed on or passing through the distal tool plate (109).

Note further that in many embodiments, at least some of the conduits comprise any of optical fibers or hollow tubes configured to convey any of optical, electromagnetic, or radiofrequency (RF) signals or chemicals to or from devices disposed on the distal tool plate (109).

Figure 13:
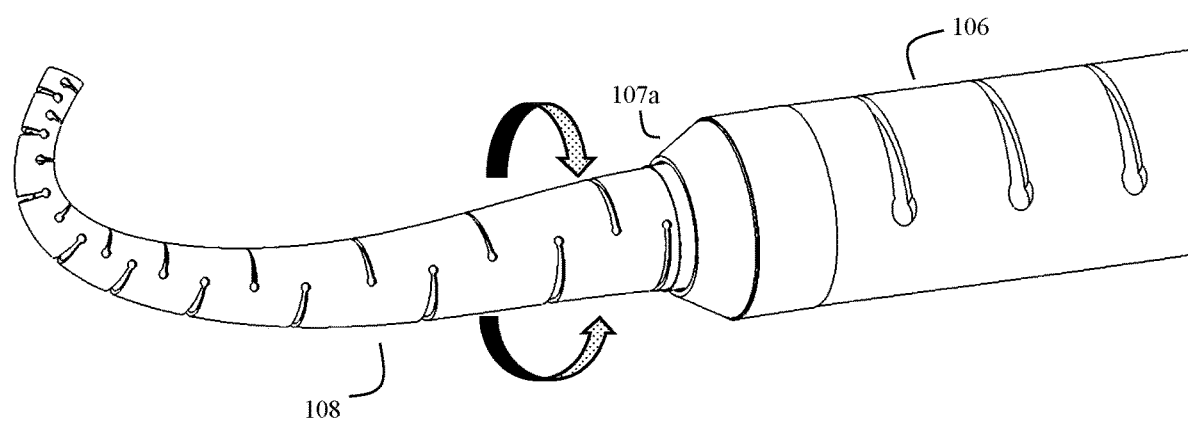
FIG. 13 shows the Distal Stage as 2-way produced from a tapered laser cut tube

FIG. 13 shows that in some embodiments, the distal stage (106) may be produced from a tapered tube, such as a tapered laser cut tube. This embodiment can be useful to help scale the distal stage (108) to a patient's individualized anatomy, both in diameter, length, and shape of curvature. See FIG. 39 and FIG. 40 for further discussion.

More specifically, in some embodiments, at least the distal stage hollow catheter (108) may be tapered from a larger external diameter at the hollow rotatable coupler (107*a*, 107*b*) to a smaller external diameter at a distal end (at or near the distal plate 109) of the distal stage hollow catheter. Further, the device may be configured to enable at least distal portions of the distal stage hollow catheter (108) to be maneuvered though body lumens with internal open diameters of 3 millimeters or less (see FIG. 2 and FIG. 3, 50).

Although the device disclosed herein may be used for many medical and veterinary applications, in some embodiments, the body lumens may comprise any of trachea (12), primary or secondary or tertiary bronchus or bronchi, or bronchiole (12, 14, 16, 18, 20). Here the device may be specifically configured as a bronchoscope.

Figure 14:
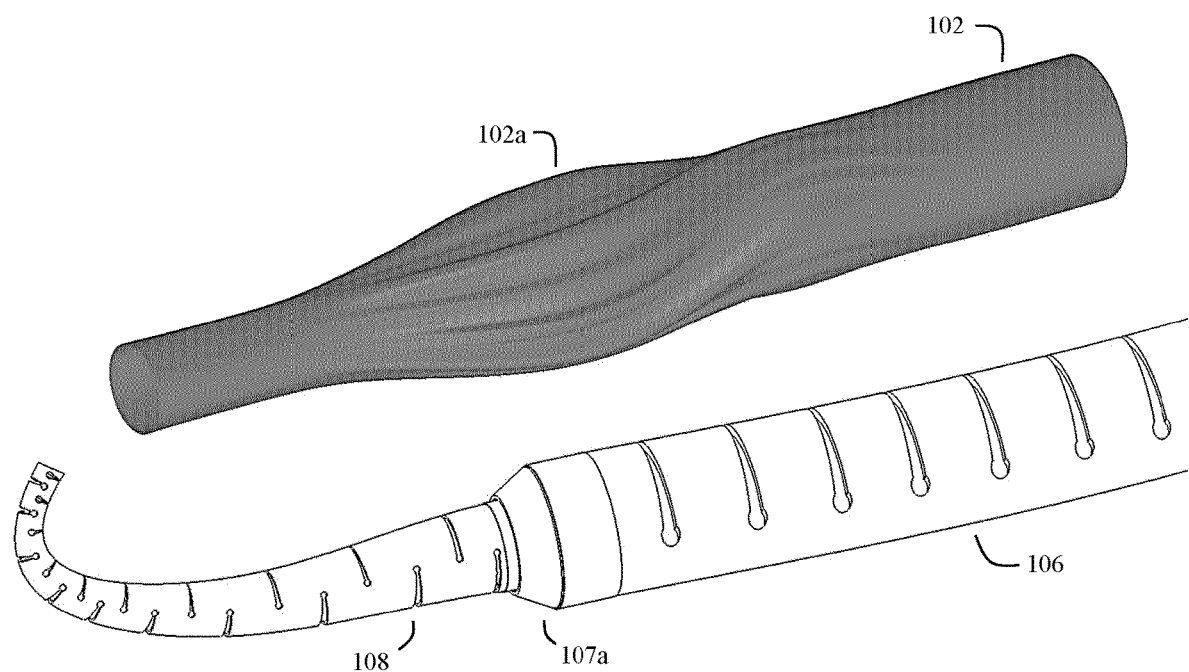
FIG. 14 shows a detail of a flexible sheath that may cover at least portions of the distal and proximal stages.

As shown in FIG. 14, in some embodiments, a flexible sheath (102) will cover at least portions of both distal and proximal stages (108, 106). This can be used in both bronchioscope applications as well as other applications such as where the device is applied to the blood stream. Other types of flexible coverings, distinct from any introducer sheath, may also be used as desired.

In the application of bronchoscopy, there can alternatively be two sheaths covering stages (106, 108), one sheath for each stage, so the the rotary portion at the transition housing (107*a* and/or 107*b*) is free to rotate in either direction without restriction. Depending on the requirements for other locations in the body, i.e. blood vessels, the sheath can be contiguous, and at the area of the transition housing (107*a*) the sheath is not adhered. This allows for an extended amount of rotation in either direction of at least 360 degrees.

FIG. 14 also shows how, in some embodiments this sheath need not be tightly adhered to the device at the area around the transition housing (107*a*). Instead, the sheath may have some slack (102*a*) at this region. This allows some degree of rotation with a single sheath design Put alternatively, in some embodiments, at least proximal portions (such as the 106 region) of the proximal stage hollow catheter may be disposed within at least one hollow sheath (102). As shown in FIG. 4, at least a portion of this at least one hollow sheath can be configured to enable at least portions of the multi-stage catheter device (either 106 or 108) to be slide (e.g., protrude or retreat inside and outside of this at least one hollow sheath (102). This can depend on forces applied to this at least one hollow sheath (102) and at least the proximal stage hollow catheter (106).

Figure 15:
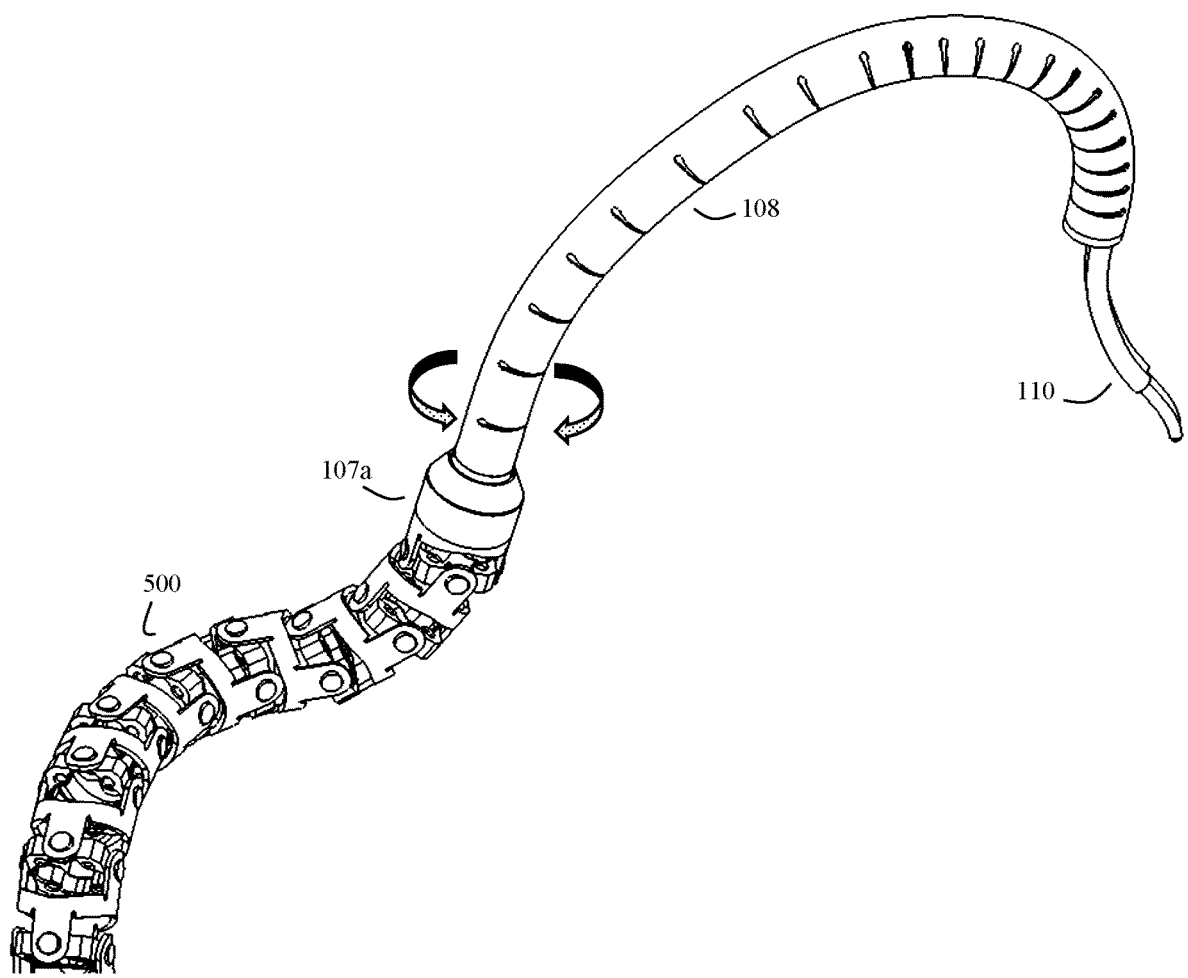
FIG. 15 shows an embodiment where the proximal stage is a 4-way type link system.

There are many combinations of flexure types for either the distal or proximal stages. FIG. 15 shows that in some embodiments, instead of being a catheter, the proximal stage may even be a 4-way link type system (500), such as that taught by Schmitz, U.S. patent application Ser. No. 18/186,176 and/or Schmitz, U.S. Pat. No. 1,103,342) coupled to a rotable 1-plane/1 direction laser cut (e.g., laser slit, or slit) hypo-tube or other type of tube for the distal stage (108). This allows for full 3D articulation (X, Y, Z axis) from a very simple 1-way device.

For steering the catheter, there can be up to 4-way (e.g. four steering cables) steering in the case of the yoke and link system (or other 4-way links) shown in the previous images. The most simplified method uses all 1-way (e.g., one steering cable) capability with the distal stage (108) having both 1-way (1 steering cable) and distal stage rotational freedom (provided by torque shaft 200) passing through the proximal stage (106).

Here the terms "1-way steering" generally mean that there is one steering cable. Similarly 2-way steering implies two steering cables, 3-way steering means three steering cables, and 4-way steering implies 4-way steering. The use of 1-way steering in some of the figures and examples is not intended to be limiting.

FIG. 16 shows a cross section of the system using a 1-way steerable introducer sheath (102) with its own steering cables (such as 102*b*), a 1-way proximal stage (106) with steering cables (such as 210) a 1-Way distal stage (108) with a hollow torque shaft (200) and its own steering cables (such as 220). Other types of conduits (230) are also shown. This produces the smallest diameter catheter at the Distal Stage with the least complex design and the most efficient DFM while pushing the performance of the device for reaching the outer third of the lungs.

Figure 17:
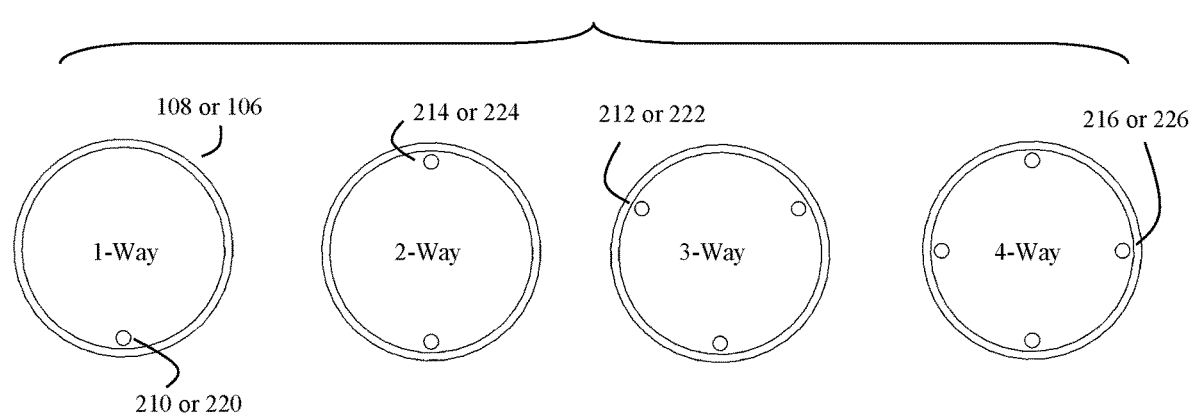
FIG. 17 shows the different pull wire orientations for each type of flexible system: 1 plane/1 direction (1-way), 1 plane/2 direction (2-way), 3 plane 3D (3-way), and 4 plane 3D (4-way).

FIG. 17 shows the different pull wire or steering cable orientations for each type of flexible system, here using either the proximal (106) or distal stage (108) cables as an example: 1 plane/1 direction (1-way), 1 plane/2 direction (2-way), 3 plane 3D (3-way), and 4 plane 3D (4-way). Technically, the 4-way has the highest degree of freedom. The 3-way is least practical. The 1-way and 2-way are most economical, and the 1-way (one steering cable) with the coupled rotational element (e.g., 200, 107*a*, and 107*b*) produces the highest performance in the smallest outside diameter where a working channel, camera, and lighting are required.

System Integration Example

Figure 18A:
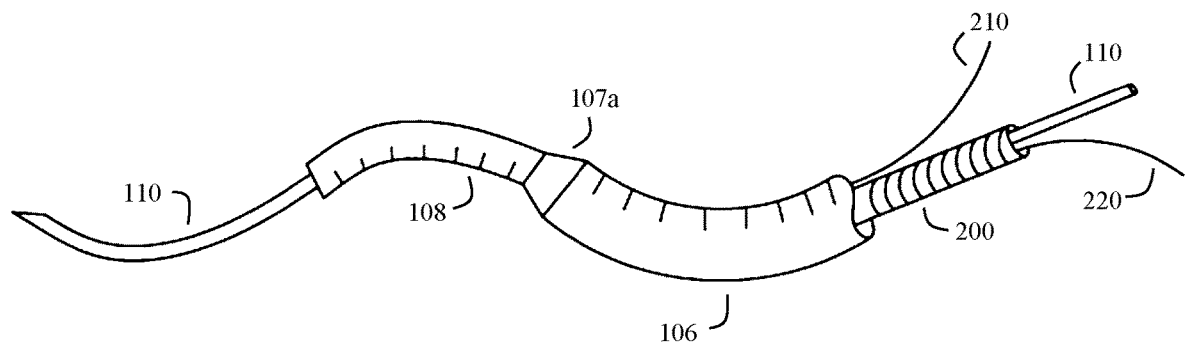
FIG. 18A, FIG. 18B, and FIG. 18C show an example of different steering cable configurations.
Figure 18B:
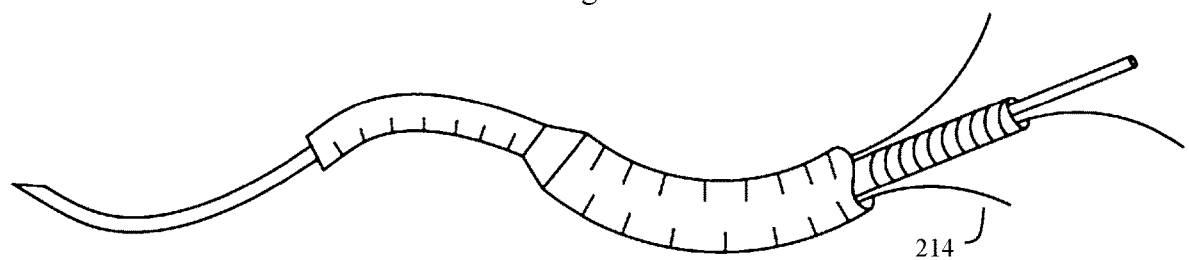
Figure 18C:
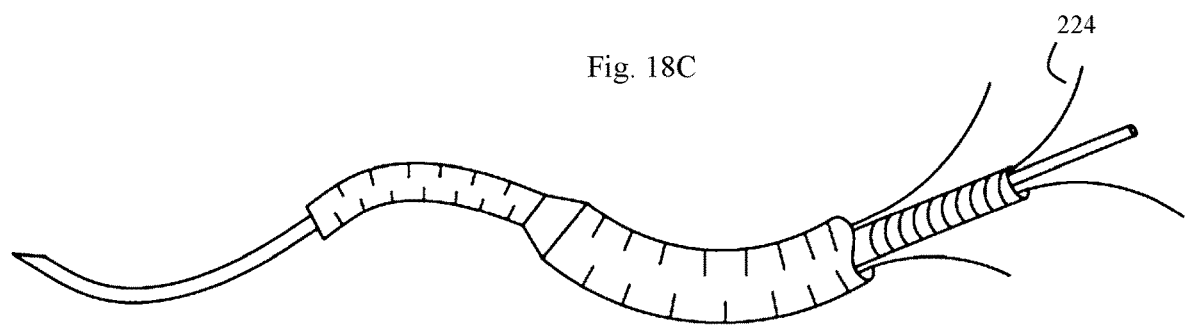

FIG. 18A, FIG. 18B, and FIG. 18C show an example of different steering cable configurations. In FIG. 18A, the proximal portion (106) has 1-way steering due to cable (210), and the distal portion (108) has 1-way steering due to cable (220). In FIG. 18B, the proximal portion has 2-way steering due to cable (210) and additional cable (214), while the distal portion still has 1-way steering. In FIG. 18C, the proximal portion (106) has 2-way steering, and the distal portion (108) now has 2-way steering due to new cable (224).

Figure 19:
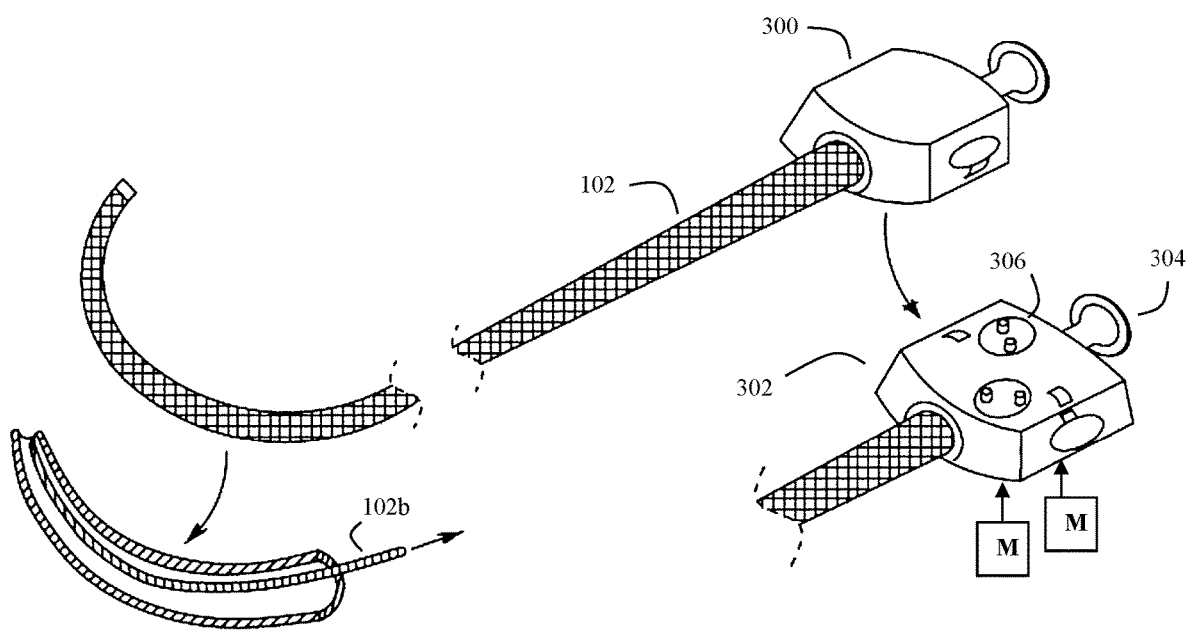
FIG. 19 shows a system example with a steerable introducer sheath control head.

FIG. 19 shows a system example of a steerable introducer sheath attached to drive cartridges for a robotic system. The first cartridge or control head (300) can actuate the introducer sheath (102) to bend/flex or rotate. This hollow sheath can be used for the delivering the rotary articulatable catheter (device). In a preferred embodiment, this sheath and control head arrangement may have at least one plane of articulation (at least 1-way steering) in at least one direction. In other embodiments, the hollow-sheath and control head may have up to full universal articulation (e.g., 4-way steering). In FIG. 19, the top figure shows the outside of the control head/sheath system, while the lower figure shows some of the mechanisms inside the control head/sheath system, such as a sheath articulation cable 102*b* and various drive wheels (306) and motors (M), often referred to as actuators (306) that can be used to manipulate the one or more sheath articulation cables.

In other embodiments, the "sheath" can comprise a mechanism that collapses but does not buckle.

FIG. 19 also shows that the articulation introducer sheath can have at least one plane and one direction of articulation (here using sheath articulation cable 102*b*) with an axis of rotation located at the control head housing (300, 302).

Put alternatively, in some embodiments, the multi-stage catheter device can further comprise at least one control head (300). This at least one control head may comprise a hollow introducer sheath (102) and insertion funnel (304), configured to admit at least portions of the multi-stage catheter device (e.g., 106, 107, 108, 109), through the insertion funnel and hollow introducer sheath, and into a body lumen.

Figure 20:
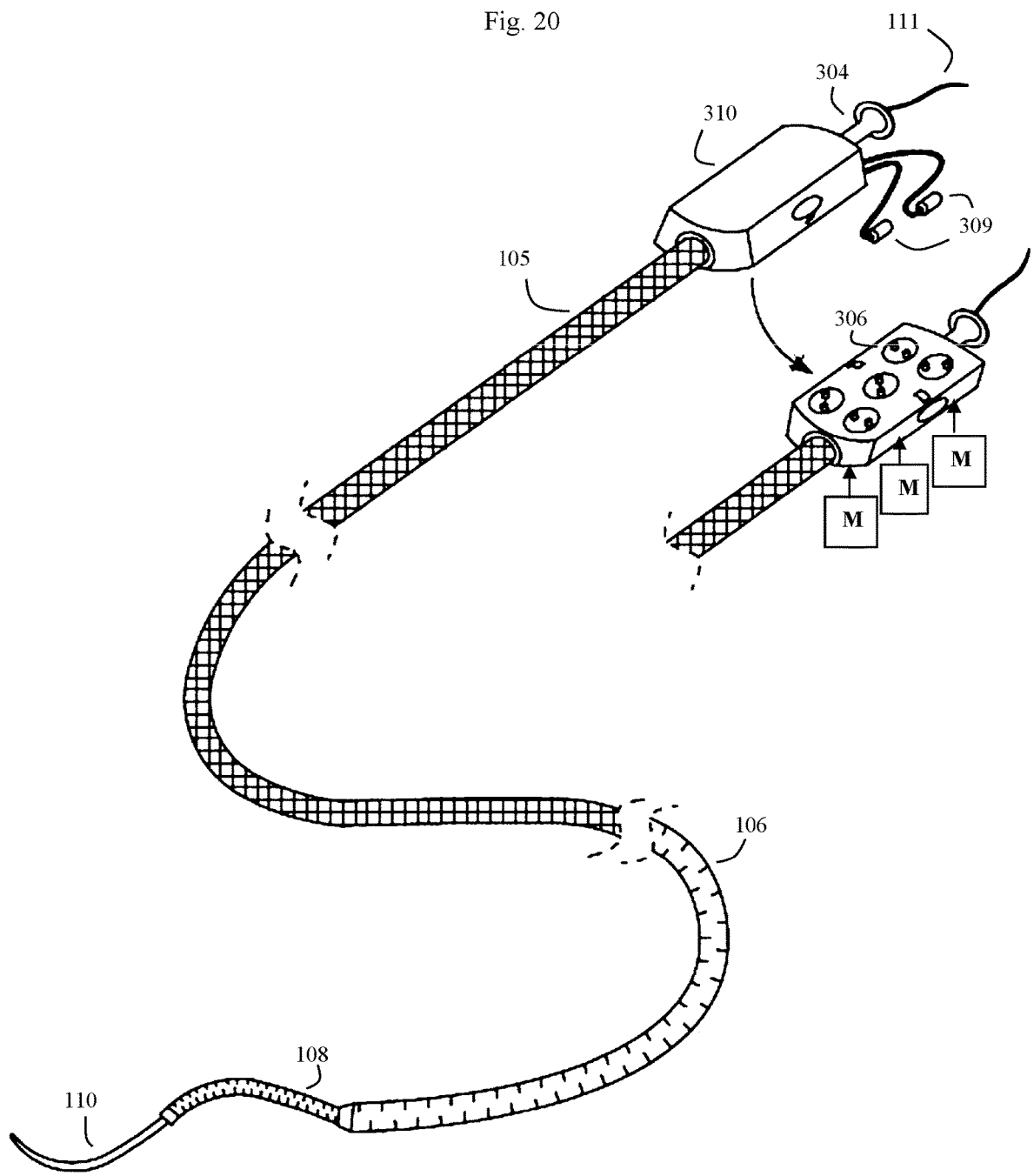
FIG. 20 shows another example of the articulating rotary robotic bronchoscope control head.

FIG. 20 shows an alternative embodiment of the articulating rotary robotic bronchoscope device control head, here designated as (310), showing other portions of the device, such as an extreme proximal portion (105) that connects to the proximal portion (106), the distal portion (108), and other portions. (Here, (105) can be viewed as an extreme proximal portion of the device that may have different flexibility than the proximal region (106), and although configured to be flexible, need not be necessarily be configured to be steerable.) A conduit (111) that connects to the tool tip (110) after passing through insertion funnel (304) is also shown. This control head may also have additional drive wheels (306) and motors (M), often referred to as actuators, which are often processor controlled motorized actuators, which are used to control other articulation/steering cables. Other devices shown (309) are connectors and interfaces to operate and control other conduits, such as cameras controlling cameras, lights, sensors, position indicators, electrodes, tool tips, and the like. Note that for simplicity, the introducer sheath is not shown.

Thus, in some embodiments, the at least one control head (300, 310) may be further configured with at least one computerized drive wheel (306) and motor (M), often called a motor actuator, or sometimes just an actuator. This at least one computerized motor actuator may be configured to perform any of:

Apply variable torque to the hollow torque shaft (200); and/or

Apply variable tension to any of the at least one proximal stage steering cable (210) and/or at least one distal stage steering cable (220); and/or As per the FIG. 19 introducer sheath discussion, also apply variable tension to at least one sheath steering cable (102b) disposed inside the hollow introducer sheath (102).

Although the various actuators, such as the previously discussed drive wheel (306) and motor (M) arrangements, may be part of the control head (300 or 310), in some embodiments, the actuator system may have some actuator components, such as the drive wheels (306) mounted on the control heads (300, 310), and have other components, such as the motors (M), mounted on a robotic system, such as a robotic arm.

Note that in some embodiments, the systems shown in FIGS. 19 and 20 may be configured to be either disposable or reposable (able to be recycled a limited number of times) and will often be delivered pre-sterilized and in sterile packaging. The drive wheels (306) can be part of the disposable or reposable system, and the motors (M) that interface with the drive wheels may be configured as part of the durable medical equipment (such as part of a robotic system). After installation, the motor portions (M) may attach and detach from the drive wheels (306).

Figure 21:
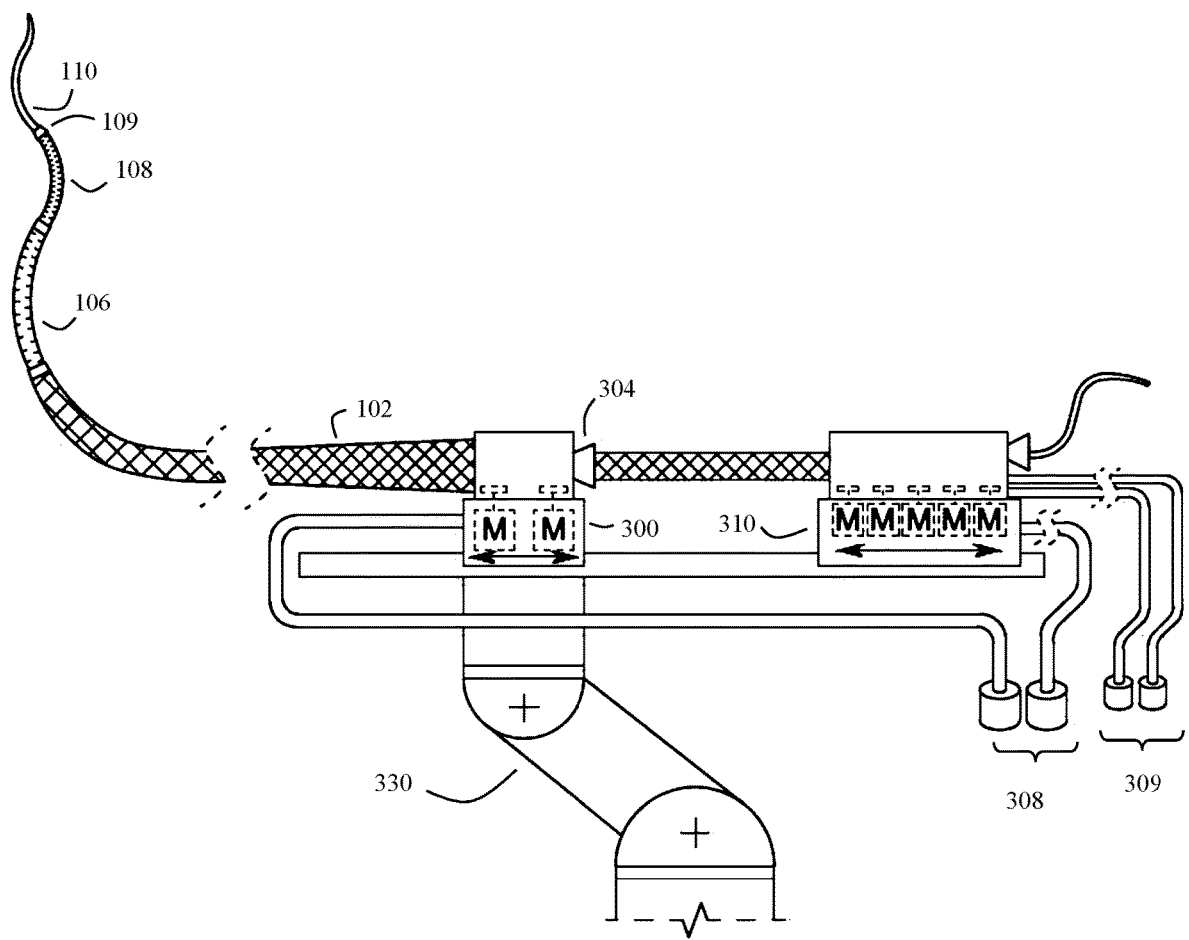
FIG. 21 shows the device implemented on a robotic system where both steerable sheath and steerable bronchoscope control heads are mounted and move independently of each other.

FIG. 21 shows the device implemented on a robotic system where are two control heads (300, 310), both are mounted (here on a robotic arm 330), containing blocks of motors "M" that can interface with the drive wheels (306) on the control heads. In this configuration, both control heads are are configured to move independently of each other, and along the same axis.

In FIG. 21, the computerized motor actuator system comprises two control heads (300, 310). These are mounted on the processor controlled robotic arm (330). This processor controlled robotic arm is further configured to move the catheter/bronchoscope device, and control a computerized motor actuator system (such as previously discussed drive wheels 306, and motors "M") to guide at least the distal tool plate (109) of the distal end of the distal stage hollow catheter (108) to a target location. Here (308) shows the connectors and/or position encoders to control any of motors "M" as well as other motors to control the robotic arm's linear stages. As before, (309) shows the connectors and interfaces to operate and control other conduits, such as cameras controlling cameras, lights, sensors, position indicators, electrodes, tool tips, and the like.

Figure 22:
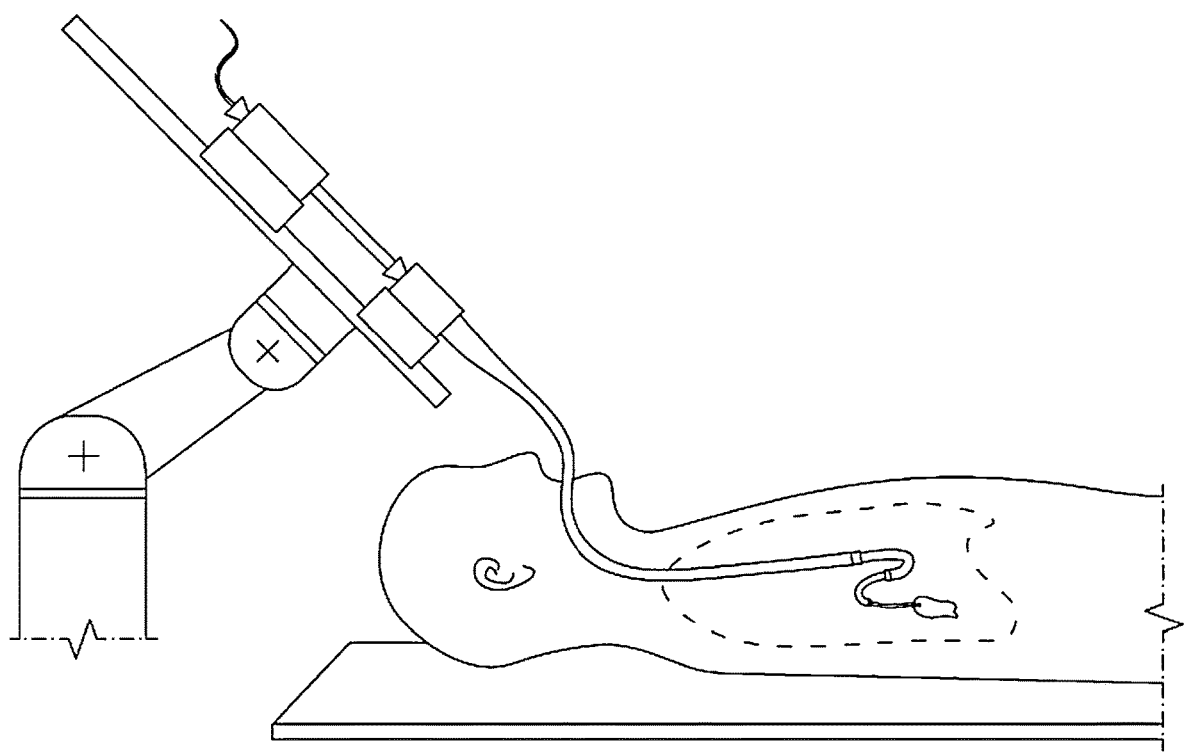
FIG. 22 shows an embodiment where the robotic system is applying the catheter to a patient.

FIG. 22 shows an embodiment where the robotic system is applying the catheter to a patient.

In some embodiments, the at least one control head is mounted on a processor controlled robotic arm. This processor controlled robotic arm is further configured to move the device and control the at least one computerized motor actuator. These are used to guide at least the distal tool plate of the distal end of the distal stage hollow catheter to a target location (inside the patient).

Figure 23A:
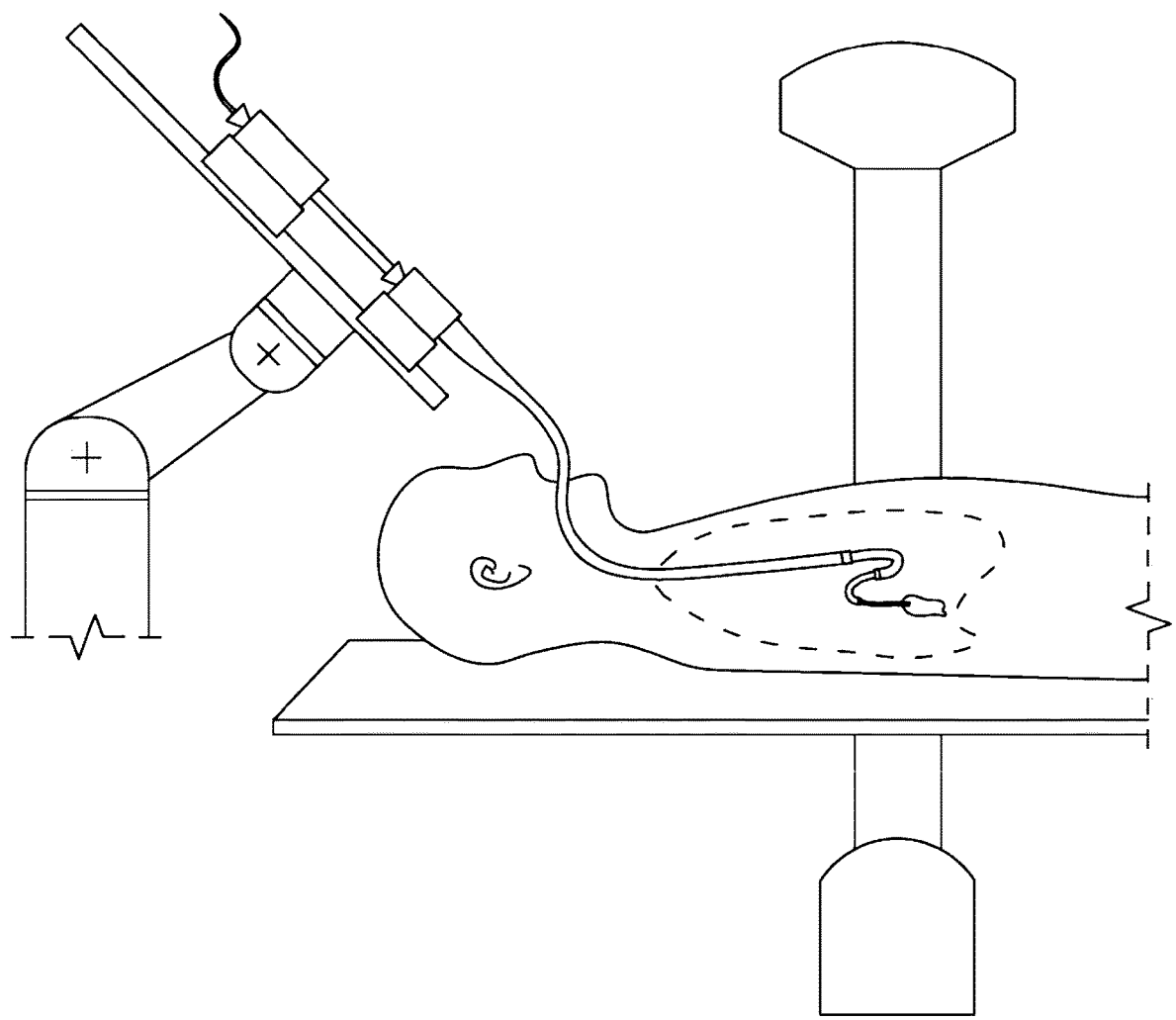
FIG. 23A shows an embodiment where the robotic system is applying the catheter to a patient, using a C-arm type imaging system to visualize progress.

FIG. 23A shows an embodiment where the robotic system is applying the catheter to a patient, here using a C-arm mounted radiologic imaging system to help visualize progress.

Figure 23B:
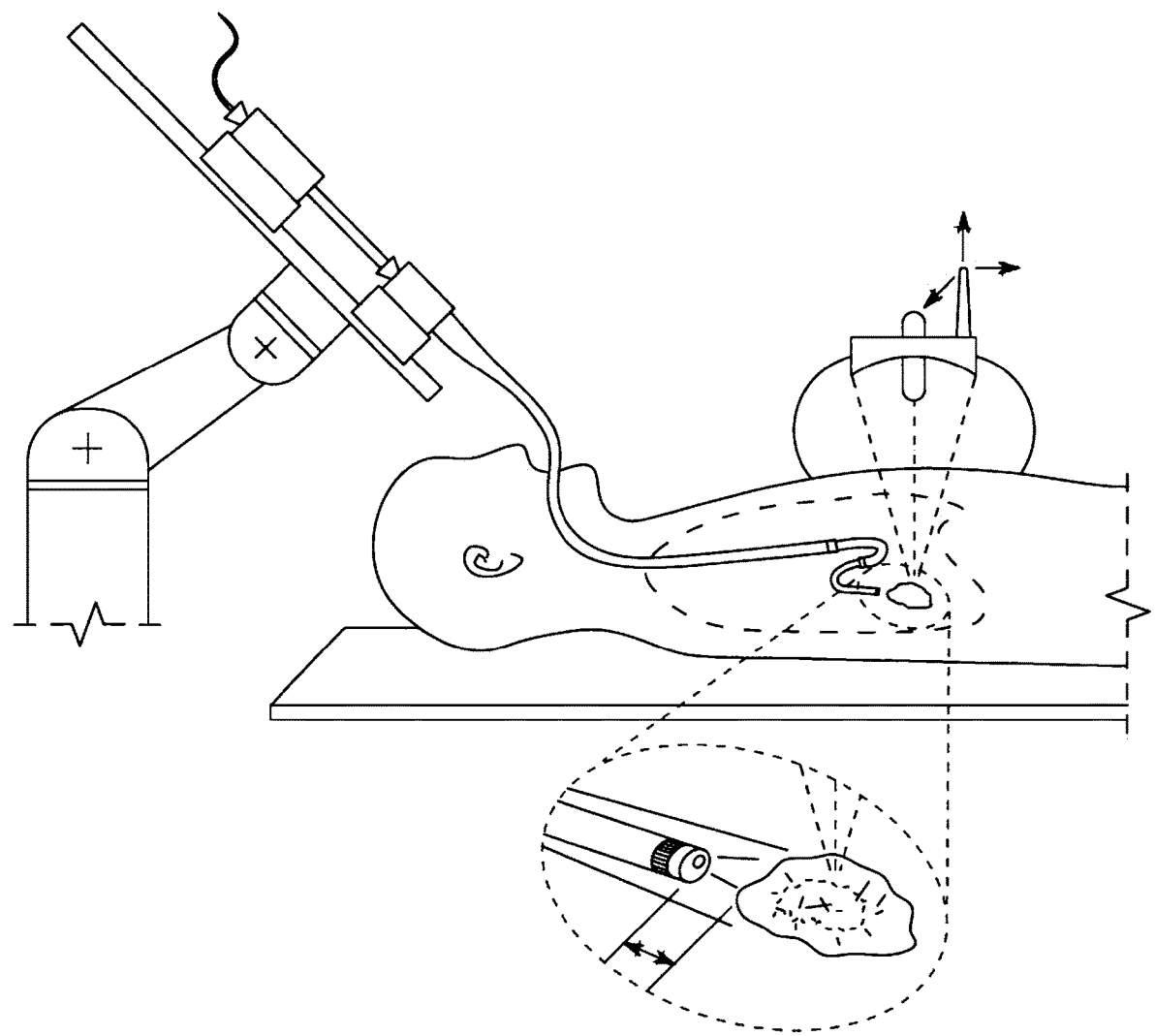
FIG. 23B shows an alternate embodiment where the robotic system is further configured to administer therapeutic energy, such as ultrasonic energy, to a target tissue.

FIG. 23B shows an alternate embodiment where the robotic system is also configured to deliver therapeutic energy, such as ultrasonic, infrared, or other type of energy to a target tissue. Here the device may be used for multiple purposes, such as directing the therapeutic energy, delivering agents to enhance the therapeutic impact of the therapeutic energy, or assess the results of the therapy.

Figure 23C:
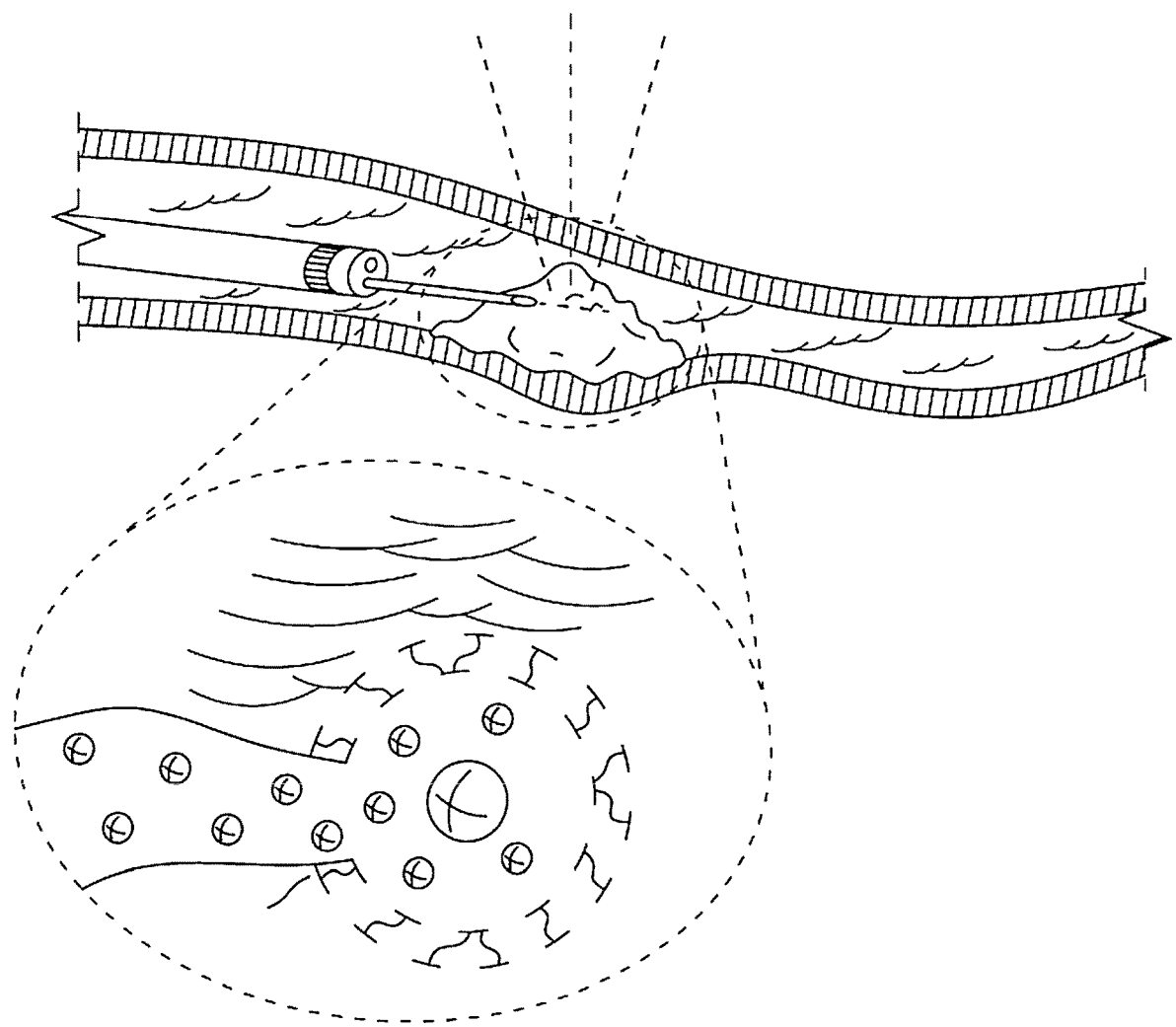
FIG. 23C shows an alternate embodiment where the robotic system is also configured to administer an imaging contrast agent or one or more therapeutic molecules to a target tissue.

FIG. 23C shows an alternate embodiment where the robotic system is also configured to administer an imaging contrast agent or one or more therapeutic molecules to a target.

The Distal Tool Head (Distal Plate)

Figure 24:
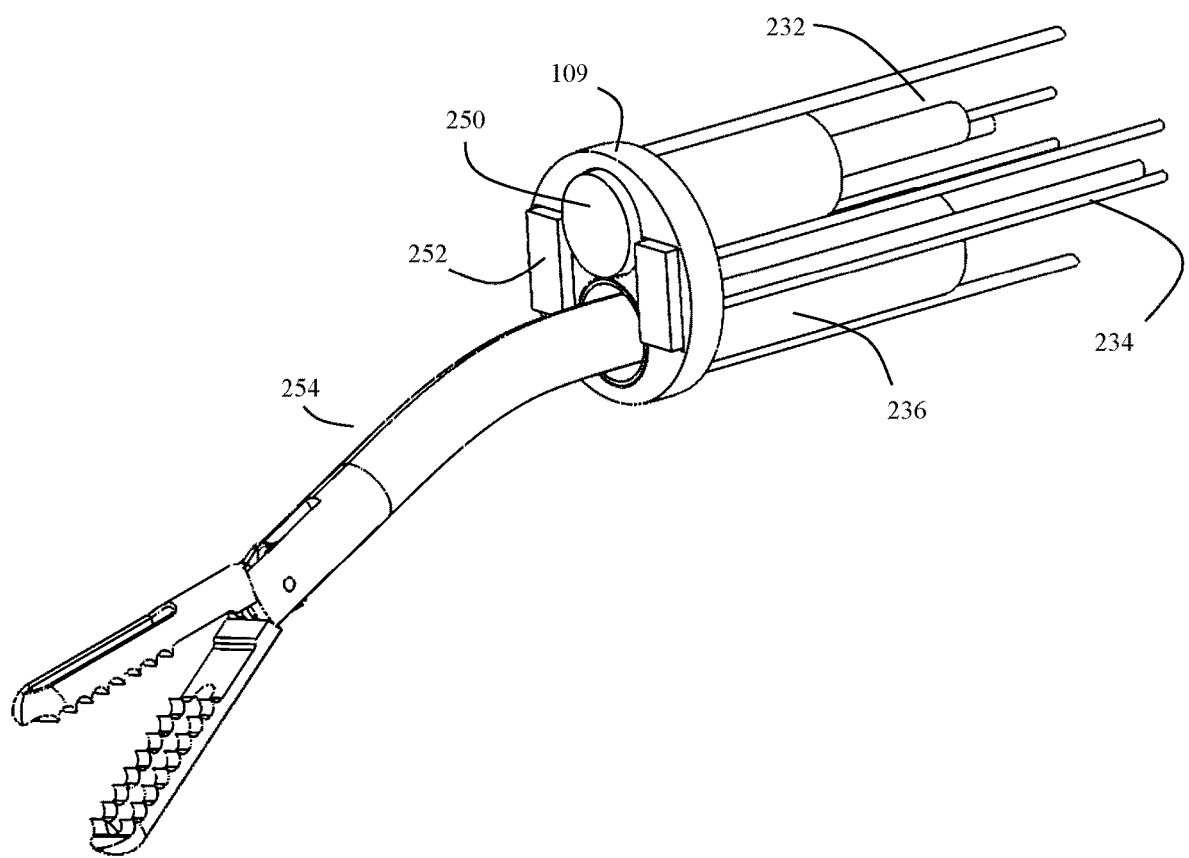
FIG. 24 shows the tool head with camera, lighting and forceps.

The distal stage (distal portion 108) often has a tool head (109) at its distal end. Although the examples so far have mostly just shown electrodes (110) as one type of tool, many alternative tools and configurations are also possible. As shown in FIG. 24, this tool head (109) may be alternatively, or additionally, fitted with other devices such as a camera, lighting and a tube or opening for delivering tools, e.g. forceps, brushes, biopsy needles, electrodes, drug delivery needles, and the like.

Although usually the distal tool plate will obscure at least some part of the distal opening of the distal stage hollow catheter (108), alternative embodiments are possible. In some embodiments, distal tool plate (109) may be configured with a distal tool plate opening diameter that is as large as an inner diameter of the distal stage hollow catheter (108). Note that this large-opening distal tool plate will still be configured to attach to the steering cables (220 . . . 226).

FIG. 24 shows the distal tool plate (aka tool head 109) with camera (250), lighting (252) (such as the two LED lights shown) and forceps. Here the outer wall of the distal portion (108) is not shown (or alternatively it has been made transparent) so that the various components and conduits (210-240) can be seen.

For example, camera (250) may be serviced by a first electrical conduit (232), LED (252) may be served by a second or third electrical conduit (234). The conduits may also include hollow tubes (236), from which various devices, such as forceps (254) may be routed and controlled.

Figure 25:
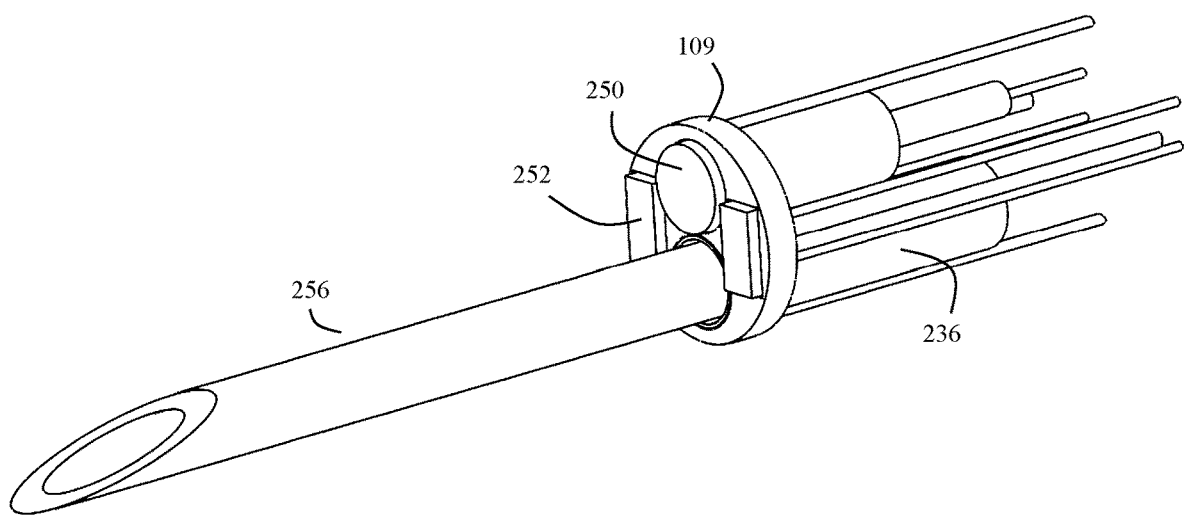
FIG. 25 shows the tool head with a biopsy needle.

FIG. 25 shows the tool head (109) with a biopsy needle (256).

Put alternatively, in some embodiments, at least some of the conduits (such as 236) and the distal tool plate (109) may be configured to obtain any of tissue biopsies from a target tissue, or to administer therapy to a target tissue.

Figure 26:
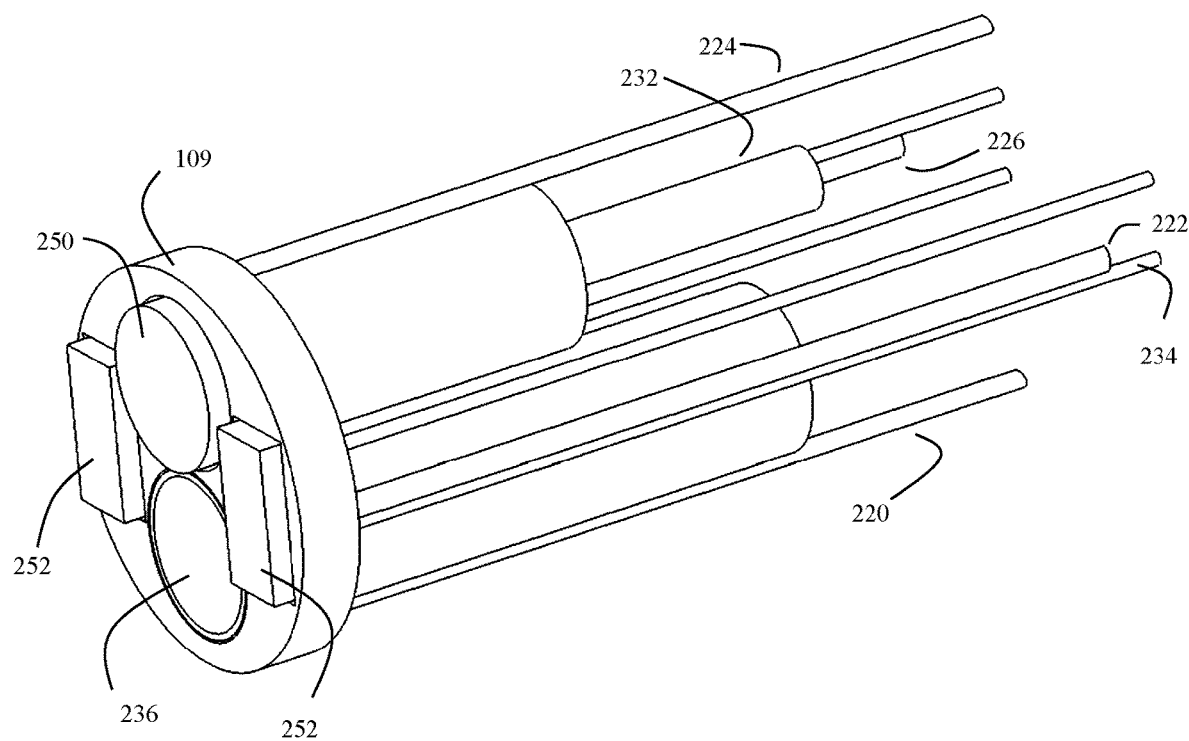
FIG. 26 shows some of the components that may be integrated into the tool head's tool plate.

FIG. 26 shows another view of some of the components and conduits that may be integrated into the tool head's tool plate (109). In here this includes a camera 250), a working channel (which can also be viewed as a hollow tube conduit (236) for delivering tools, and two LED lights (252). Coming off the tool plate (109) are the four previously discussed pull wires, conduits, or cables (220, 222, 224, and 226) for a 4-way distal stage articulation (e.g., X, Y, and Z axis movement, or 3D articulation). The conduit leads (232), (234) for the camera and LEDs are also shown. The camera (250) can be any type of small video camera, including a CMOS, CCD, or fiberscope. The LEDs (252) can be replaced by fiber optics lighting as desired, in which case some of the conduits (such as 234) may be optical fibers.

As previously discussed in FIGS. 22 to 23B, it will often be useful to use various types of location tracking or imaging devices to determine the location of the device, in particular the tool plate (109) and/or associated tools while in use. Thus, in some embodiments, any of the distal tool plate (109) or portions of the conduits may comprise any of optical or radiofrequency detectors or emitters or radioopaque materials configured to enable a location of the distal tool plate or portions of the conduits to be determined.

As previously discussed, often the optical detector (250) may be a video camera, and the emitter (such as 252) may be configured to emit light for this video camera.

Figure 27:
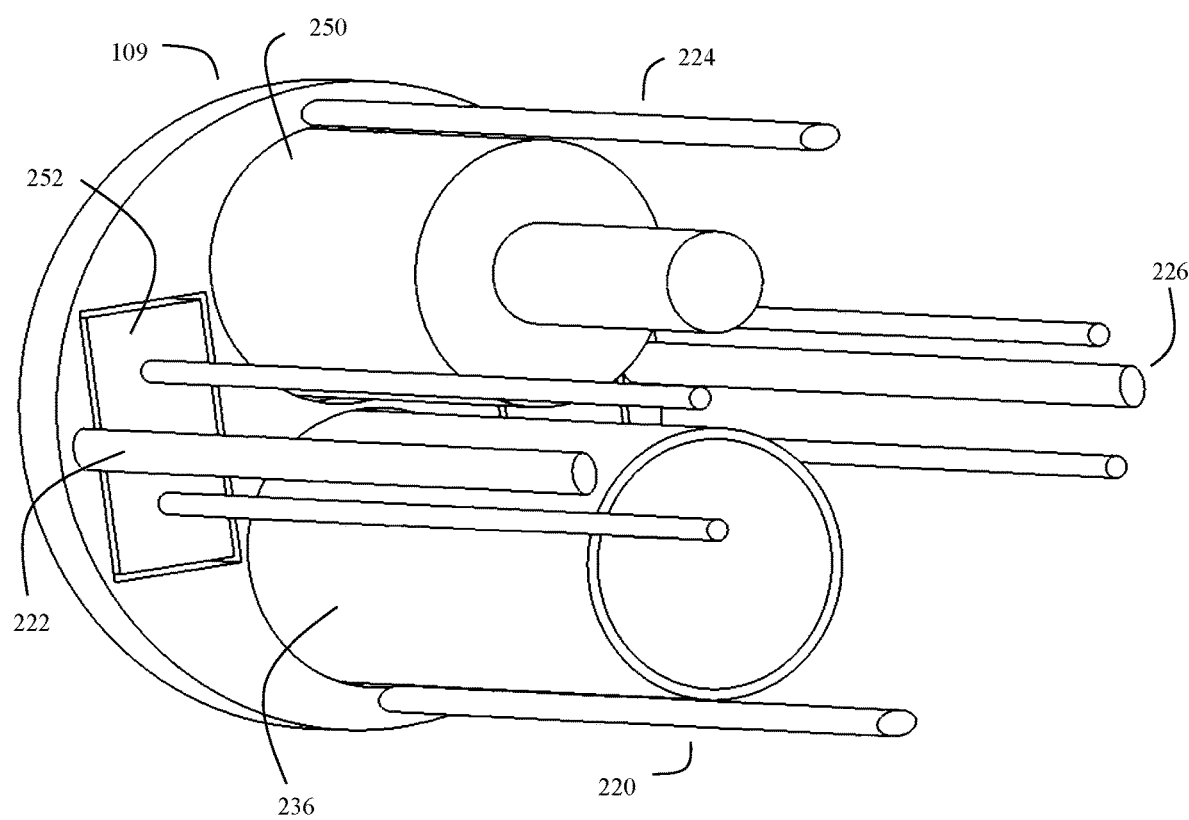
FIG. 27 shows the backside of one embodiment of the the tool head

FIG. 27 shows the backside of one embodiment of the the tool head (109). The pull wires (steering cables, conduits) in this case are for a 4-way, but they can be reduced down to 3, 2, or 1-way steering arrangement.

Distal Plate Features:

The distal plate, also called the distal tool plate (109) is a main structural component, often disk shaped, that is positioned on the distal end of the distal segment (108). The distal tool plate holds various types of conduits that send electrical or chemical signals to and from the distal end of the device and the operator or computer at the proximal end of the device. The distal tool plate can also provide access for tools to reach the area of treatment.

Figure 28:
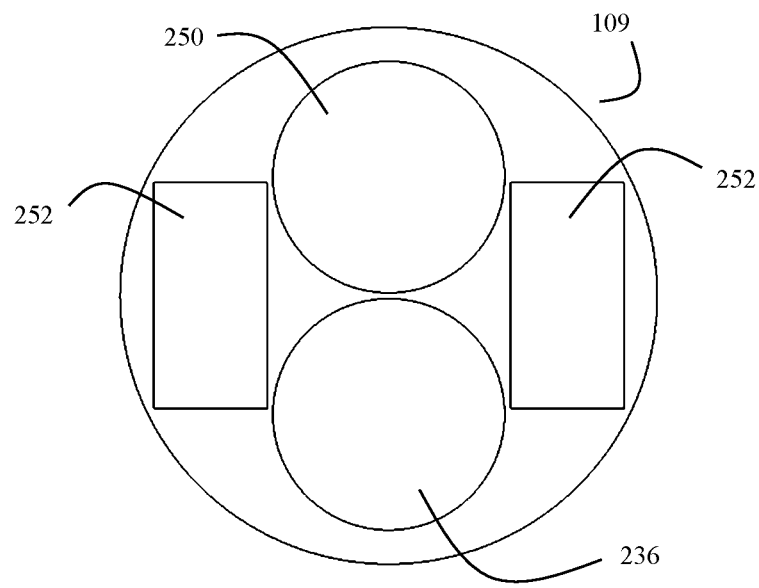
FIG. 28 shows an embodiment of the tool plate that locates and mounts a camera, two LEDs light and a tool port.

FIG. 28 shows an embodiment of the tool plate (109) that locates and mounts a video camera (250), two LEDs to provide light (252), and a hollow tube conduit (236) that can be used as a tool port.

Figure 29:
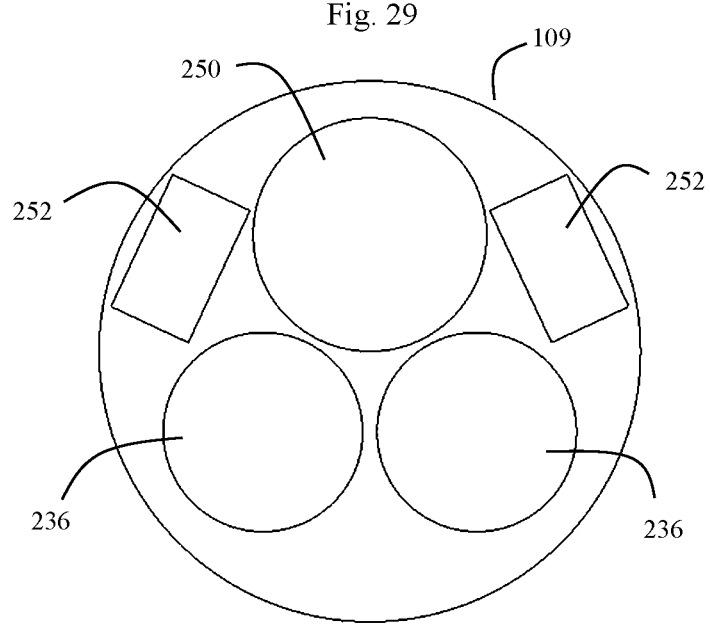
FIG. 29 shows the tool plate with two tool ports, camera and LEDs.

FIG. 29 shows the tool plate (109) with two hollow tube conduits (236) providing two tool ports, a camera (250) and two LEDs (252).

Figure 30:
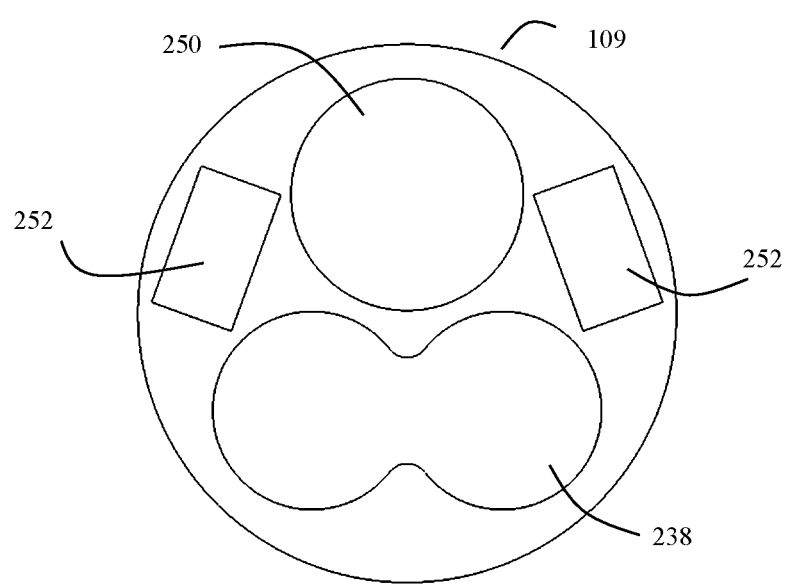
FIG. 30 shows the tool plate with a tool port with guide feature for bipolar electrodes or other tools plus camera and LEDs.

FIG. 30 shows the tool plate (109) with a tool port (238) providing another type of conduit that can provide a guide feature to introduce bipolar electrodes (such as (110*a* and 110*b*), or other tools, plus a camera (250) and LEDs (252).

Methods of Biopsy, and Delivering Therapy at the Tool Head

Figure 31A:
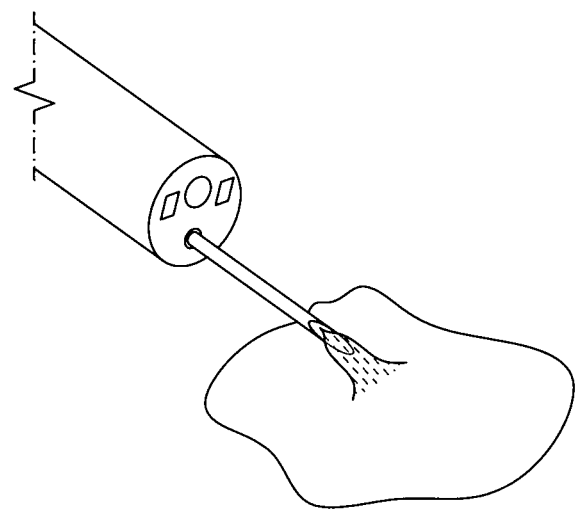
FIG. 31A and FIG. 31B shows that a needle can be used to retrieve a biopsy from a lesion location using the Articulating Rotary Robotic Bronchoscope.
Figure 31B:
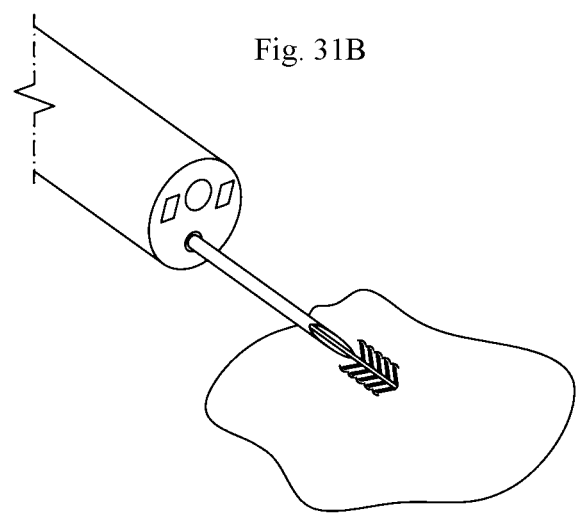

FIG. 31A and FIG. 31B shows how a needle can be used to retrieve a biopsy from a lesion location using the catheter device.

Figure 32:
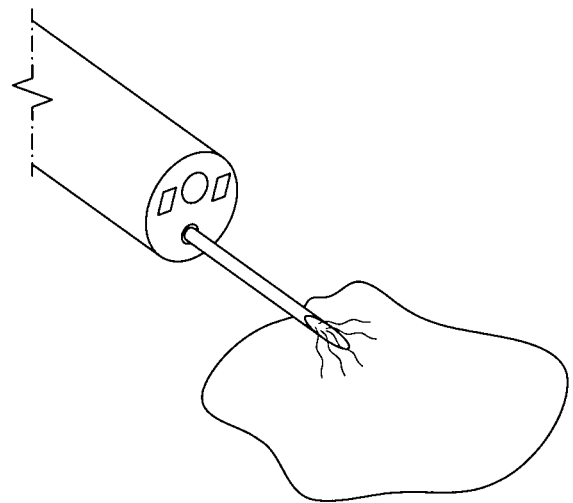
FIG. 32 shows an example of monopolar treatment methods, such as using the device to inject a drug into a cancerous tumor.

FIG. 32 shows an example of monopolar therapy methods (here defined as providing therapy using only one probe), such as using the device to inject a drug into a cancerous tumor.

Figure 33:
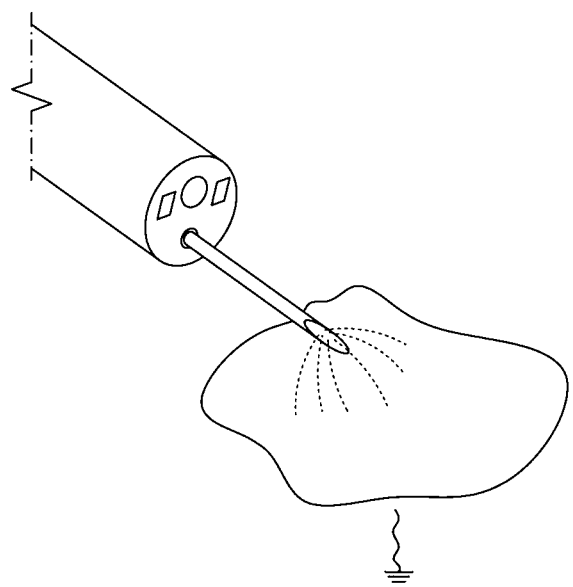
FIG. 33 shows another example of monopolar methods, here treating a cancerous tumor with radiofrequency (RF) mono-polar energy to either treat or activate a drug.

FIG. 33 shows another example of monopolar therapy methods, here treating a cancerous tumor with radiofrequency (RF) mono-polar energy from a single electrode to either treat the tumor directly, or activate a drug that in turn attacks the tumor.

Figure 34:
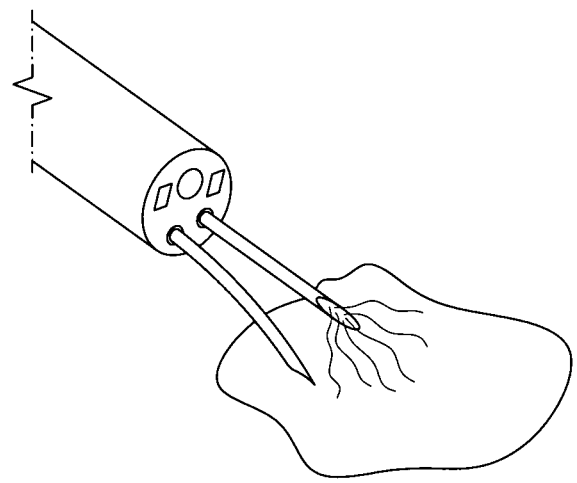
FIG. 34 shows an example of a Bi-polar method. Here a drug can be injected into a cancerous tumor. There is a return needle that is also injected into the tumor.

FIG. 34 shows an example of a bi-polar therapy method, here defined as providing therapy using two probes). Here a drug can be injected into a cancerous tumor using a first probe or needle. There is a return needle that is also injected into the tumor, which may either be used to deliver a second drug, more of the first drug, or return excess drug from the tumor.

Figure 35:
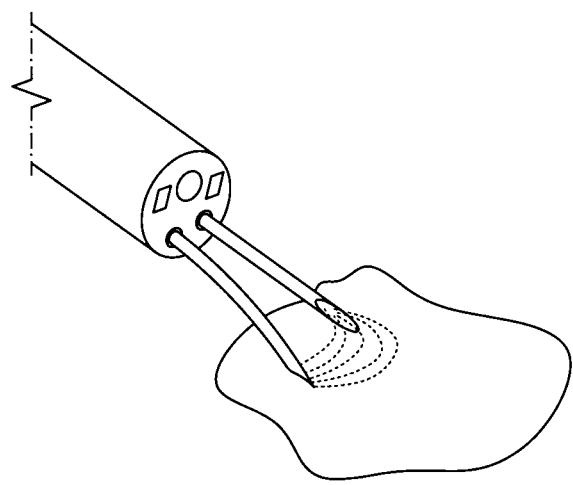
FIG. 35 shows another example of a Bi-polar method. Here the cancerous tumor can be treated with RF bi-polar energy to either treat or activate a drug.

FIG. 35 shows another example of a bi-polar therapy method. Here a cancerous tumor can be treated with RF (radiofrequency) energy between two electrodes to either treat the tumor directly, or activate a drug to in turn attack the tumor.

Figure 36:
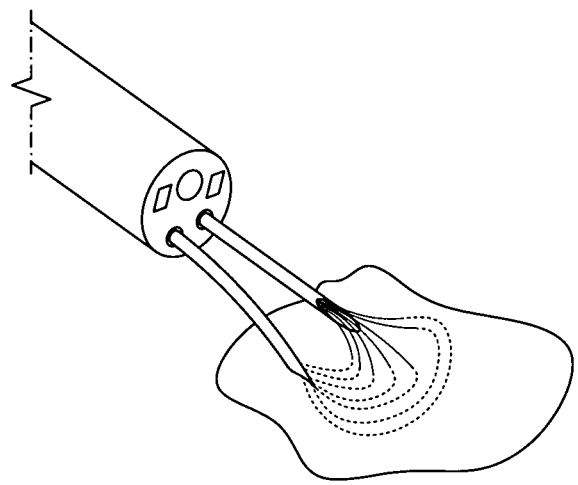
FIG. 36 shows an example of using bipolar RF energy to treat tumor by activating a therapeutic. In this case the plurality of needles are spread out in to the tumor

FIG. 36 shows an example of using bipolar RF energy to treat a tumor by activating a therapeutic. In this case two (or more) electrode needles are spread out into the tumor.

Figure 37:
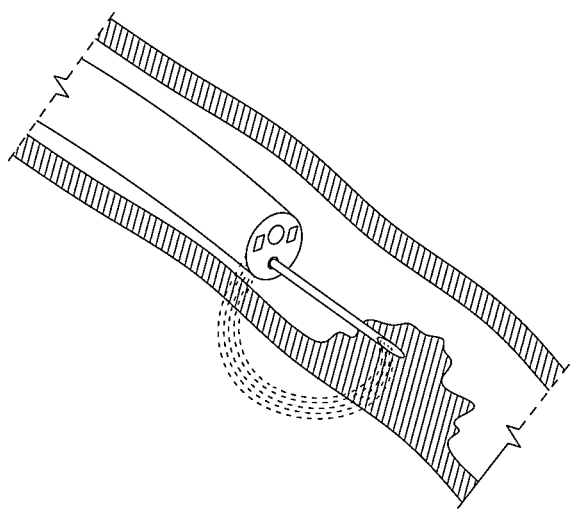
FIG. 37 shows that a tumor can be injected with a single needle and bi-polar RF energy can return through the body of the catheter where an electrode can be exposed at the front of the catheter.

FIG. 37 shows that a tumor can be injected with a single needle, and this same needle can act as a first electrode to deliver RF energy. Here, the head plate (109) or the body of the catheter (108) can act as a second electrode. Thus, with this arrangement, an electrode can be exposed at the front of the catheter, and bi-polar RF energy can return through the body of the catheter.

Drive Methods, Crawling

In some embodiments, the catheter can be made to crawl through tissue (see FIG. 1-3 as an example) with an undulating wave which can be set up between the distal (108) and proximal (106) flexing stages. This motion, along with the rotation of the distal stage (induced by hollow shaft 200) can produce a crawling or serpentine like movement. With the spinning distal stage while also flexing, the stage can drive further into a body lumen (such as a vessel or bronchi) towards the desired target. This is shown in FIG. 38A and FIG. 38B.

FIG. 38B shows an example of a robotic drive motion in schematic form that, usually in conjunction with one or more processors, drives the actuators/motors (often in a control head) to create this type of wave between the distal (108) and proximal stages (106). While this is happening, the hollow shaft (200) can also cause the distal stage (108) to rotate about the hollow rotatable coupler (107*b*) and transition housing (107*a*), causing the distal stage (108) to both rotate and thread itself into the bronchus or other body lumen.

1. In some embodiments, the two-stage robotic catheter can be made to crawl based on an algorithm that is driven by a known pre-operation 3D-map of the patient's pathway anatomy and the real-time position based on CT or MM data.
2. In some embodiments, the algorithm can be configured to drive the previously discussed two-stage catheter where the proximal stage (106) is configured to bend (using proximal stage steering cables such as 210) and also to be pushed by a driving robot (see FIG. 21), and the distal (108) stage both bends (using distal stage steering cables such as 220) and rotates (due to hollow torque shaft 200, the rotatable coupler 107*b*, and the transition housing 107*a*) in the opposite direction of the proximal stage.

3. In some embodiments, the catheter device can be made to crawl by creating an undulating wave. This can be done by configuring the appropriate actuators to flex the distal (108) and proximal stages (106) out of phase with one another, thus producing a serpentine movement. In addition, as discussed above, the distal stage (108) can also be driven to rotate while flexing. With the distal stage rotating while at the same time flexing, the stage can drive further into the vessel, bronchi, or other body lumen.

Further Discussion

Any of the following instruments may pass through the device to a distal end effector at the device's distal end: cameras and lighting; needle biopsy devices; brush biopsy devices; forceps biopsy devices; debrider biopsy devices; RF coagulation/cutting devices (monopolar, bipolar); probes; sealing devices; and the like. Similarly, the joints and devices described herein may be used or adapted for use in any suitable medical or surgical procedure, including but not limited to: debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures (TURP, bladder tumors) prostatectomy, hysterectomy, stem cell delivery, delivery of arthroscopic tools, knees and hips, and transnasal procedures (frontal sinus tissue removal, functional endoscopic sinus surgery, etc.). These are only examples, however, and any other end effectors and procedures may be used in various alternative embodiments.

Methods of Manufacturing

As previously discussed in FIG. 11 and FIG. 13, in some embodiments, the invention may also be a method of producing the multi-stage catheter device described herein. As previously discussed, this device may comprise a distal stage hollow catheter (108) and a proximal stage hollow catheter (106), one end of this distal stage hollow catheter affixed to an end of the proximal stage hollow catheter by a hollow rotatable coupler (107*b*) and transition housing (107*a*) configured to enable the one end of the distal stage hollow catheter (108) to rotate with respect to the end of the proximal stage hollow catheter (106).

The device will typically further comprise a hollow torque shaft (200) mounted inside the proximal stage hollow catheter. This hollow torque shaft is usually configured (200) to convey torque to the distal stage hollow catheter (108).

The device further comprises at least one proximal stage steering cable (such as 210) connected to the transition housing (107*a*). This at least one proximal stage steering cable (210) is disposed inside the proximal stage hollow catheter (106), but outside the hollow torque shaft (200). This at least one proximal stage steering cable (210, 212, 214, 216) enabled to convey proximal stage steering force on the transition housing (107*a*). This causes the transition housing (107*a*) and the distal stage hollow catheter (108) to move according to the proximal stage steering force.

The hollow torque shaft (200), distal stage hollow catheter (108), hollow rotatable coupler (107*b*) and the transition housing (107*a*) are hollow. That is, they further comprise a working channel configured to convey a plurality of conduits through the proximal stage hollow catheter and the distal stage hollow catheter to at least a distal tool plate (109), which is mounted on a distal end of the distal stage hollow catheter (108).

At least some of these conduits comprise at least one distal stage steering cable (such as 220, see also 222, 224, 226) connected to the distal tool plate (109) on the distal end of the distal stage hollow catheter (108).

These at least one distal stage steering cable(s) (220) are configured/enabled to convey distal stage steering force on or to the distal tool plate (109). This causes the distal tool plate (109) and the distal stage catheter (108) to further move according to the various distal stage steering forces.

Note further that in some embodiments, any of the distal stage hollow catheter (108) and the proximal stage hollow catheter (106) may further comprise a plurality of slits or flexure relief patterns (such as 108*a*, 106*a*) positioned along at least a portion of their circumference. These slits may have positions and dimensions that are configured to facilitate catheter traversal through a series of branching body lumens of progressively smaller internal diameters, as per FIG. 1 to FIG. 3. Note further that both the distal stage hollow catheter (108) has a distal stage length, and the proximal stage hollow catheter (106) has a proximal length. In some embodiments, any of these lengths may be customized to also facilitate catheter traversal through a series of branching body lumens of progressively smaller internal diameters Here, the method for constructing such a device, which is particularly useful for making custom catheters precisely attuned to the biometric characteristics of a given patient, can further comprise using a medical scanner (see FIG. 39, 602) to scan a patient (600), thus obtaining lumen pathway data (similar to the lung pathways shown in FIG. 1 to FIG. 3). The method then uses at least one design processor to determine fabrication instructions, as well as using these fabrication instructions to construct at least portions of the multi-stage catheter device (such as 108, 106, 109, 107, etc.). Here, for example, any of the stage lengths and slit positions may be customized.

Figure 39:
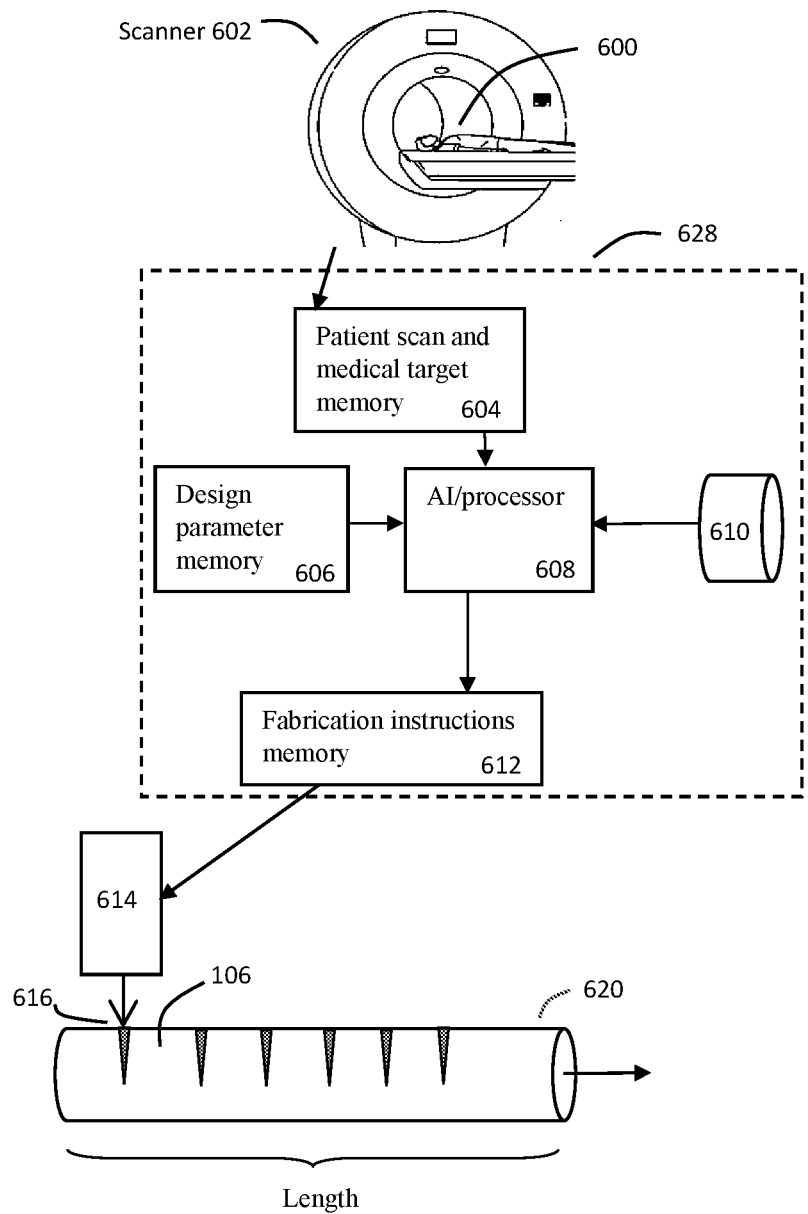
FIG. 39 shows an example of some of the equipment that may be used to automatically produce at least portions of the device.

FIG. 39 shows an example of some of the equipment that may be used to automatically produce at least portions of the surgical device, such as entire units or at least portions of the units.

The method can be implemented according to various options.

In some embodiments, the surgical device may be customized for a particular patient. In other embodiments, a range of more standardized surgical devices may be created, each optimized for a different class of patients or class of surgical targets. If a given patient and surgical target can be adequately covered by an available standardized surgical device, then the standardized surgical device may be used. If not, then a customized surgical device may be created. Here, let us assume that the patient needs a customized surgical device.

For a customized surgical device, it will often be useful to acquire specific data pertaining to the structural dimensions of that patient's body lumen or other internal body passage intended for that surgical pathway. The location of the surgical target will also be needed. In this example, assume that this data is acquired by a suitable medical imaging scan, such as a CAT or CT scan, MRI scan, ultrasonic scan, X-ray, or another modality (602).

As shown in FIG. 39, to do this, the patient (600) may be scanned by a medical imaging scanner (602). The resulting medical image scan data (which may be annotated to point out the desired surgical pathway and target) is transferred into computer memory (604). Additional data, such as the design parameters for the desired surgical device may also be transferred (if it is not previously present) into computer memory (606). This information is then processed by at least one computer processor (608). This at least one computer processor can be chosen from the ARM, x86, MIPS or other processor families, and in some embodiments may be further comprise additional AI (artificial intelligence) hardware such as specialized neural net or AI processors (NPU), Graphics processors (GPU), FPGA (field programmable gate arrays), and co-processors. Examples of suitable NPU and GPU processors include the Intel NCS2 chip, Telum processor, Nvidia DGZ A100, Google Cloud TPU, Edge TPU, Cerebras WSE-2, and others.

The AI/processor system (608) will take the patent scan and medical target data, the design parameters relative to the type of device desired, and (often supplemented, or trained by a historical database of other devices/pathway—target situations) and determine a device that best satisfies the various constraints. See FIG. 40 for more detail.

Once the overall design is determined, either AI/processor (608) or a different AI or processor unit can then determine the fabrication instructions (612) needed to create the various components of the device. These components can include the diameters and lengths of at least some of the various units or portions of the units (106, 108, 109, and so on) and other components as desired.

These fabrication instructions (612) can also be stored in computer memory (612). In some embodiments, certain portions of at least the memory (604, 606, optionally historical database 610), the AI/processor 608 and/or fabrication instruction memory (612) may be packed as a single unit (628), often referred to here as the AI system, but such packaging is optional.

Certain portions of the device may often be based on standardized and pre-fabricated sections or units. However often other portions of the device may be customized to that particular patient/pathway/target situation. Such customization is particularly useful for the design of the distal catheter (108) and optionally the tool plate (109) so as to best fit a given patient.

In some embodiments, the fabrication instructions (612) may be used to operate various types of automated manufacturing equipment, such as CNC (computer numerical control) machining devices, computerized laser cutting devices, and the like. In FIG. 39, these instructions (612) are shown operating a laser cutter (614), which is cutting (616) various portions of the device from a stock material such as a hollow hypodermic tube (620). This tube can made from stainless steel, flexible polymer, or other surgical grade material.

After optional further processing, these portions can then be further assembled to form a completed device customized to that particular surgical pathway and target situation.

Figure 40:
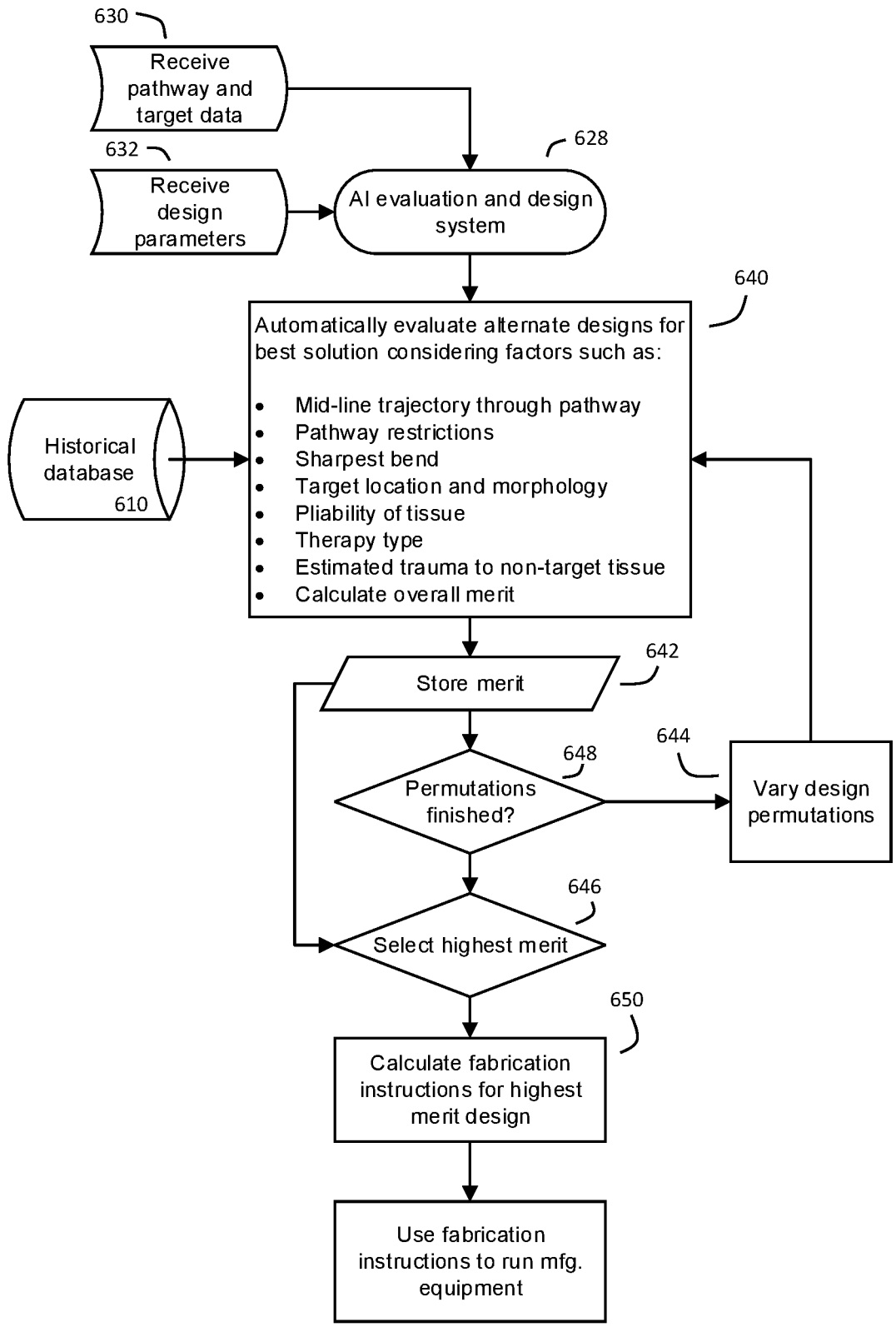
FIG. 40 shows a flow chart showing some aspects of the invention's computerized design and manufacturing methods.

FIG. 40 shows a flow chart showing some aspects of the invention's computerized design and manufacturing methods.

As previously discussed, the process will often begin by receiving pathway and target data into computer memory (604), (630). This will typically include device pathway data describing at least some structural dimensions of a patient's body lumen or other internal body passage. Additionally, the process often requires entering additional information into computer memory, such as target location data describing at least one target location (642) in the patient's body, and its location relative to the device pathway data (644).

The method also requires computer memory configured with the device design parameters (632), as previously discussed.

The method then uses at least one computer processor (e.g., AI/processor 608), the pathway data (644), at least one target location data (642), and device design parameters to automatically design a patient customized device configured to traverse a pathway between an entry point (646) on the patient's body lumen or other internal body passage, along the patient's body lumen (644) or other internal body passage, and to this at least one target location (642).

Some factors that the automated system (628) or method may consider include evaluating (either iteratively, or through AI methods), a plurality of alternate candidate device designs.

In some embodiments, for at least some of these designs, the system/method can calculate a plurality of different paths that a given candidate device may traverse along the pathway (644) between an entry point (646) and the target (642). Here, keep in mind that a different surgical device made with different sized units will often traverse somewhat different paths. The system can evaluate alternate designs (640), try different permutations (648), select the best solution (646)

For at least some of the various candidate devices, the at least one computer processor (608) can evaluate the diameters of the given candidate device along the pathway (644). The processor can also evaluate the ability of at least some of the units of a given candidate surgical device to bend along a given pathway. The processor can also evaluate the ability of at least some proximal portions (106) of the given candidate device to drive and/or guide distal portions (108) of the given candidate device as the distal units approach the target (642), and calculate fabrication instructions (650) as appropriate.

The invention claimed is:

1. A multi-stage catheter device for traversing internal body passages, said device comprising:
a distal stage hollow catheter and a different proximal stage hollow catheter;
said distal stage hollow catheter being a rotating distal stage hollow catheter with a distal stage axis that is configured to rotate about a proximal stage axis of said different proximal stage hollow catheter;
one end of said rotating distal stage hollow catheter affixed to an end of said different proximal stage hollow catheter by a transition point coupler;
said transition point coupler configured to traverse an internal body passage;
said transition point coupler comprising a transition housing that includes a hollow rotatable coupler, said hollow rotatable coupler configured as a rotary joint to enable said one end of said rotating distal stage hollow catheter to rotate about said end of said different proximal stage hollow catheter;
said device further comprising a hollow torque shaft mounted inside said proximal stage hollow catheter and attached to said hollow rotatable coupler, said hollow torque shaft configured to convey torque to said rotatable coupler and said rotating distal stage hollow catheter;
said device further comprising at least one proximal stage steering cable connected to said transition housing, said at least one proximal stage steering cable disposed inside said proximal stage hollow catheter, outside said hollow torque shaft, said at least one proximal stage steering cable enabled to convey proximal stage steering force on said transition housing, causing said transition housing and said distal stage hollow catheter to move according to said proximal stage steering force;
said hollow torque shaft, rotating distal stage hollow catheter, hollow rotatable coupler and said transition housing further comprising a working channel configured to convey a plurality of conduits through said proximal stage hollow catheter and said rotating distal stage hollow catheter to at least a distal tool plate mounted on a distal end of said rotating distal stage hollow catheter;

wherein at least some of said conduits comprise at least one distal stage steering cable connected to said distal tool plate on said distal end of said rotating distal stage hollow catheter;

said at least one distal stage steering cable enabled to convey distal stage steering force on said distal tool plate, causing said distal tool plate and said rotating distal stage catheter to further move according to said distal stage steering force.

2. The device of claim 1, wherein at least proximal portions of said proximal stage hollow catheter are disposed within at least one hollow sheath, at least one of said at least one hollow sheath configured to enable at least portions of said multi-stage catheter device to protrude or retreat inside and outside of said at least one hollow sheath, depending on forces applied to said at least one hollow sheath and at least said proximal stage hollow catheter.

3. The device of claim 1, wherein said distal tool plate is configured with an opening with a distal tool plate opening diameter as large as an inner diameter of said distal stage hollow catheter.

4. The device of claim 1, wherein said device further comprises a computerized motor actuator system configured to apply variable torque to said hollow torque shaft, and variable tension to any of said at least one proximal stage steering cable and/or at least one distal stage steering cable.

5. The device of claim 4, wherein said computerized motor actuator system is configured to operate according to an algorithm to reduce friction, while still guiding said catheter to a desired location, by repetitively lowering said variable tension to reduce friction, applying said torque to partially rotate said distal stage hollow catheter, and then reestablishing tension to guide said catheter to said desired location.

6. The device of claim 4, wherein said computerized motor actuator system is mounted on a processor controlled robotic arm, and said processor controlled robotic arm is further configured to move said device and control said computerized motor actuator system to guide at least said distal tool plate of said distal end of said distal stage hollow catheter to a target location.

7. The device of claim 1, wherein at least some of said conduits comprise electrical conduits configured to transmit any of electrical power or electrical signals to any of probes, sensors, or other electrically activated devices disposed on or passing through said distal tool plate.

8. The device of claim 1, wherein said at least some of said conduits comprise any of optical fibers or hollow tubes configured to convey any of optical, electromagnetic, or radiofrequency (RF) signals or chemicals to or from devices disposed on said distal tool plate.

9. The device of claim 1, wherein at least said distal stage hollow catheter is tapered from a larger external diameter at said hollow rotatable coupler to a smaller external diameter at a distal end of said distal stage hollow catheter; and wherein said device is configured to enable at least distal portions of said distal stage hollow catheter to be maneuvered though body lumens with internal open diameters of 3 millimeters or less.

10. The device of claim 9, wherein said body lumens comprise any of trachea, primary or secondary or tertiary bronchus or bronchi, or bronchiole, and wherein said device is configured as a bronchoscope.

11. The device of claim 1, wherein any of the distal stage hollow catheter and the proximal stage hollow catheter comprise a plurality of slits along at least a portion of their circumference;

said slits having positions and dimensions are configured to facilitate traversal of said device through a series of branching body lumens of progressively smaller internal diameters.

12. The device of claim 1, wherein any of said distal tool plate or portions of said conduits comprise any of optical or radiofrequency detectors or emitters or radio-opaque materials configured to enable a location of said distal tool plate or portions of said conduits to be determined.

13. The device of claim 12, wherein said optical detector is a video camera, and wherein said emitter is configured to emit light for said video camera.

14. The device of claim 1, wherein said multi-stage catheter device further comprises at least one control head;

at least one control head comprising a hollow introducer sheath and insertion funnel configured to admit at least portions of said multi-stage catheter device, through said insertion funnel and hollow introducer sheath, and into a body lumen.

15. The device of claim 14, wherein said at least one control head is further configured with at least one computerized motor actuator; said at least one computerized motor actuator configured to apply variable torque to said hollow torque shaft and perform any of:

a) apply variable tension to any of said at least one proximal stage steering cable and/or at least one distal stage steering cable;

b) apply variable tension to at least one sheath steering cable disposed inside said hollow introducer sheath.

16. The device of claim 15, wherein said at least one control head is mounted on a processor controlled robotic arm, and said processor controlled robotic arm is further configured to move said device and control said at least one computerized motor actuator to guide at least said distal tool plate of said distal end of said distal stage hollow catheter to a target location.

17. The device of claim 1, wherein at least some of said conduits and said distal tool plate are configured to obtain any of tissue biopsies from a target tissue, or to administer therapy to a target tissue.

18. A method of producing a multi-stage catheter device for traversing internal body passages;

said device comprising:

a distal stage hollow catheter and a different proximal stage hollow catheter;

said distal stage hollow catheter being a rotating distal stage hollow catheter with a distal stage axis that is configured to rotate about a proximal stage axis of said different proximal stage hollow catheter, one end of said rotating distal stage hollow catheter affixed to an end of said different proximal stage hollow catheter by a transition point coupler;

said transition point coupler configured to traverse an internal body passage;

said transition point coupler comprising a transition housing that includes a hollow rotatable coupler, said hollow rotatable coupler configured to act as a rotary joint to enable said one end of said rotating distal stage hollow catheter to rotate about said end of said different proximal stage hollow catheter;

said device further comprising a hollow torque shaft mounted inside said proximal stage hollow catheter and attached to said hollow rotatable coupler, said hollow torque shaft configured to convey torque to said rotatable coupler and said rotating distal stage hollow catheter;

said device further comprising at least one proximal stage steering cable connected to said transition housing, said at least one proximal stage steering cable disposed inside said proximal stage hollow catheter, outside said hollow torque shaft, said at least one proximal stage steering cable enabled to convey proximal stage steering force on said transition housing, causing said transition housing and said distal stage hollow catheter to move according to said proximal stage steering force;

said hollow torque shaft, rotating distal stage hollow catheter, hollow rotatable coupler and said transition housing further comprising a working channel configured to convey a plurality of conduits through said proximal stage hollow catheter and said rotating distal stage hollow catheter to at least a distal tool plate mounted on a distal end of said rotating distal stage hollow catheter;

wherein at least some of said conduits comprise at least one distal stage steering cable connected to said distal tool plate on said distal end of said rotating distal stage hollow catheter;

said at least one distal stage steering cable enabled to convey distal stage steering force on said distal tool plate, causing said distal tool plate and said rotating distal stage catheter to further move according to said distal stage steering force;

said method comprising scanning a patient, obtaining lumen pathway data;

using at least one design processor to determine fabrication instructions; and using said fabrication instructions to construct at least portions of said multi-stage catheter device.

19. The method of claim 18, wherein any of the distal stage hollow catheter and the proximal stage hollow catheter comprise a plurality of slits along at least a portion of their circumference;

said slits having positions and dimensions are configured to facilitate traversal of said device through a series of branching body lumens of progressively smaller internal diameters; and wherein said fabrication instructions comprise any of a length of said distal stage hollow catheter and a length of said proximal stage hollow catheter, or a position of at least some of said slits along any of distal stage hollow catheter and said proximal stage hollow catheter.

20. A multi-stage catheter device, said device comprising:

a distal stage hollow catheter and a proximal stage hollow catheter, one end of said distal stage hollow catheter affixed to an end of said proximal stage hollow catheter by a hollow rotatable coupler and transition housing configured to enable said one end of said distal stage hollow catheter to rotate with respect to said end of said proximal stage hollow catheter;

said device further comprising a hollow torque shaft mounted inside said proximal stage hollow catheter, said hollow torque shaft configured to convey torque to said distal stage hollow catheter;

said device further comprising at least one proximal stage steering cable connected to said transition housing, said at least one proximal stage steering cable disposed inside said proximal stage hollow catheter, outside said hollow torque shaft, said at least one proximal stage steering cable enabled to convey proximal stage steering force on said transition housing, causing said transition housing and said distal stage hollow catheter to move according to said proximal stage steering force;

said hollow torque shaft, distal stage hollow catheter, hollow rotatable coupler and said transition housing further comprising a working channel configured to convey a plurality of conduits through said proximal stage hollow catheter and said distal stage hollow catheter to at least a distal tool plate mounted on a distal end of said distal stage hollow catheter;

wherein at least some of said conduits comprise at least one distal stage steering cable connected to said distal tool plate on said distal end of said distal stage hollow catheter;

said at least one distal stage steering cable enabled to convey distal stage steering force on said distal tool plate, causing said distal tool plate and said distal stage catheter to further move according to said distal stage steering force;

wherein said device further comprises a computerized motor actuator system configured to apply variable torque to said hollow torque shaft, and variable tension to any of said at least one proximal stage steering cable and/or at least one distal stage steering cable; and wherein said computerized motor actuator system is configured to operate according to an algorithm to reduce friction, while still guiding said catheter to a desired location, by repetitively lowering said variable tension to reduce friction, applying said torque to partially rotate said distal stage hollow catheter, and then reestablishing tension to guide said catheter to said desired location.

* * * * *